US008435773B2

(12) United States Patent
Worden et al.

(10) Patent No.: US 8,435,773 B2
(45) Date of Patent: May 7, 2013

(54) CUSTOMIZABLE AND RENEWABLE NANOSTRUCTURED INTERFACE FOR BIOELECTRONIC APPLICATIONS

(75) Inventors: Robert M. Worden, Holt, MI (US); Robert Y. Ofoli, Okemos, MI (US); Brian L. Hassler, Lake Orion, MI (US); Neeraj Kohli, East Lansing, MI (US); Ilsoon Lee, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1119 days.

(21) Appl. No.: 11/914,340

(22) PCT Filed: May 10, 2006

(86) PCT No.: PCT/US2006/018083
§ 371 (c)(1),
(2), (4) Date: Jun. 18, 2008

(87) PCT Pub. No.: WO2007/078315
PCT Pub. Date: Jul. 12, 2007

(65) Prior Publication Data
US 2009/0130698 A1    May 21, 2009

Related U.S. Application Data

(60) Provisional application No. 60/679,922, filed on May 10, 2005.

(51) Int. Cl.
| C12N 11/00 | (2006.01) |
| C12N 11/16 | (2006.01) |
| C12Q 1/34  | (2006.01) |
| C12Q 1/00  | (2006.01) |
| C12Q 1/26  | (2006.01) |

(52) U.S. Cl.
USPC ............ 435/174; 435/18; 435/25; 435/283.1; 435/287.1; 204/403.14

(58) Field of Classification Search .................. None
See application file for complete search history.

(56) References Cited

U.S. PATENT DOCUMENTS
7,291,256 B2    11/2007   Teodorczyk et al.
2004/0050717 A1*  3/2004   Teodorczyk et al. ...... 205/777.5

FOREIGN PATENT DOCUMENTS
WO    WO-2007078315 A2    7/2007

OTHER PUBLICATIONS

Loew, N., Scheller, F.W., Wollenberger, U. (2004) Characterization of Self-Assembling of Glucose Dehydrogenase in Mono- and Multilayers on Gold Electrodes. Electroanalysis 16, No. 13-14, pp. 1149-1154.*

Loew, et al. (2004) Characterization of Self-Assembling of Glucose Dehydrogenase in Mono- and Multilayers on Gold Electrodes. Electroanalysis, 16, No. 13-14, pp. 1149-1154.*

Zayats, et al. (2002) J. Am. Chem. Soc. vol. 124, pp. 14724-14735.*

"International Application Serial No. PCT/US2006/018083, International Search Report and Written Opinion mailed Apr. 17, 2008", 9 pgs.

Loew, "Characterization of Self-Assembling of Glucose Dehydrogenase in Mono and Multilayers on Gold Electrodes", Electroanalysis, 16 (13-14), (Jul. 2004), 1149-1154.

Degani, Y. et al, "Direct Electrical Communication between Chemically Modified Enzymes and Metal Electrodes. 1. Electron Transfer from Glucose Oxidase to Metal Electrodes via Electron Relays, Bound Covalently to the Enzyme", The Journal of Physical Chemistry, Mar. 12, 1987, vol. 91, No. 6, pp. 1285-1289.

Schuhmann, Wolfgang, et al, "Electron Transfer between Glucose Oxidase and Electrodes via Redox Mediators Bound with Flexible Chains to the Enzyme Surface", Journal of the American Chemical Society, 1991, vol. 113, pp. 1394-1397.

Heller, Adam, "Electrical Wiring of Redox Enzymes", Acc. Chem. Res., 1990, vol. 23, No. 5, pp. 128-134.

Raitman, Oleg A. et al, "Electrical contacting of glucose dehydrogenase by the reconstitution of a pyrroloquinoline quinone-functionalized polyaniline film associated with an Au-electrode: an in situ electrochemical SPR study", Chemical Communications, 2002, pp. 1936-1937.

Willner, Itamar et al, "Electrical Wiring of Glucose Oxidase by Reconstitution of FAD-Modified Monolayers Assembled onto Au-Electrodes", Journal of the American Chemical Society, 1996, vol. 118, No. 42, pp. 10321-10322.

Keinan, Ehud et al, "Thermostable Enzymes in Organic Synthesis. 2. Asymmetric Reduction of Ketones with Alcohol Dehydrogenase from Thermoanaerobium brockii", Journal of the American Chemical Society, 1986, vol. 108, No. 1 pp. 162-169.

Bradshaw, Curt W. et al, "A *Pseudomonas* sp. Alcohol Dehydrogenase with Broad Substrate Specificity and Unusual Stereospecificity for Organic Synthesis", Journal of Organic Chemistry, 1992, vol. 57, No. 5, pp. 1526-1532.

Bradshaw, Curt W. et al, "Lactobacillus kefir Alcohol Dehydrogenase: A Useful Catalyst for Synthesis", Journal of Organic Chemistry, 1992, vol. 57, No. 51, pp. 532-1536.

Fjeld, Clark C. et al, "Differential binding of NAD+ and NADH allows the transcriptional corepressor carboxyl-terminal binding protein to serve as a metabolic sensor", Proceedings of the National Academy of Sciences of the United States of America, Aug. 5, 2003, vol. 100, No. 16, pp. 9202-9207.

(Continued)

*Primary Examiner* — Chris R Tate
*Assistant Examiner* — Russell Fiebig
(74) *Attorney, Agent, or Firm* — Clark IP Law, PLC

(57) ABSTRACT

A chemical composite useful for preparing a bioelectronic device includes a biologically active compound, such as an enzyme, that is bound directly or indirectly to a polyelectrolyte, which can be reversibly coupled to a chemically treated electrically conductive substrate by electrostatic forces to provide biomimetic sensors, catalyst systems, and other devices having an electrode that can be regenerated and reused. Required or desired cofactors, mediators or the like may be incorporated into the devices, typically by bonding them to the treated substrate and/or the polyelectrolyte.

10 Claims, 7 Drawing Sheets

OTHER PUBLICATIONS

Prodromidis, Mamas I. et al, "Enzyme Based Amperometric Biosensors for Food Analysis", Electroanalysis, 2002, vol. 14, No. 4, pp. 241-261.

Blaedel, W. J. et al, "Study of the Electrochemical Oxidation of Reduced Nicotinamide Adenine Dinucleotide", Analytical Chemistry, Jul. 1975, vol. 47, No. 8, pp. 1337-1343.

Schmakel, Conrad O. et al, "Nicotinamide Adenine Dinucleotide (NAD+) and Related Compounds. Electrochemical Redox Pattern and Allied Chemical Behavior", Journal of the American Chemical Society, Sep. 3, 1975, vol. 97, No. 18, pp. 5083-5092.

Zayats, Maya et al, "Electrical Contacting of Flavoenzymes and NAD(P)+ -Dependent Enzymes by Reconstitution and Affinity Interactions on Phenylboronic Acid Monolayers Associated with Au-Electrodes", Journal of the American Chemical Society, 2002, vol. 124, No. 49, pp. 14724-14735.

Schmidt, Hanns-Ludwig et al, "Coenzyme Properties of NAD+ Bound to Different Matrices through the Amino Group in the 6-Position", European Journal of Biochemistry, 1976, vol. 67, pp. 295-302.

Pariente, F. et al, "Electrocatalysis of NADH Oxidation with Electropolymerized Films of 3,4-Dihydroxybenzaldehyde", Analytical Chemistry, 1994-12-01, vol. 66, No. 23, pp. 4337-4344.

Zhao, Chuan et al, "Scanning Electrochemical Microscopy of Quinoprotein Glucose Dehydrogenase", Analytical Chemistry, Jun. 1, 2004, vol. 76, No. 11, pp. 3145-3154.

Ramanavicius, Arunas et al, "Polypyrrole-Entrapped Quinohemoprotein Alcohol Dehydrogenase. Evidence for Direct Electron Transfer via Conducting-Polymer Chains", Analytical Chemistry, Aug. 15, 1999, vol. 71, No. 16, pp. 3581-3586.

Pogorelova, Svetiana P. et al, "Analysis of NAD(P)+/NAD(P)H Cofactors by Imprinted Polymer Membranes Associated with Ion-Sensitive Field-Effect Transistor Devices and Au-Quartz Crystals", Analytical Chemistry, Feb. 1, 2003, vol. 75, No. 3, pp. 509-517.

James, Tony D. et al, "Novel Saccharide-Photoinduced Electron Transfer Sensors Based on the Interaction of Boronic Acid and Amine", Journal of the American Chemical Society, 1995, vol. 117, No. 35, pp. 8982-8987.

Berg, Michael C. et al, "Tailored Micropatterns through Weak Polyelectrolyte Stamping", Langmuir, 2003, vol. 19, No. 6, pp. 2231-2237.

Clark, Sarah L. et al, "The Role of Secondary Interactions in Selective Electrostatic Multilayer Deposition", Langmuir, 2000, vol. 16, No. 26, pp. 10206-10214.

Burdette, Douglas S. et al, "Cloning and expression of the gene encoding the Thermoanaerobacter ethanolicus 39E secondary-alcohol dehydrogenase and biochemical characterization of the enzyme", Biochemical Journal, 1996, vol. 316, pp. 115-122.

Weibel, Michael K. et al, "The Glucose Oxidase Mechanism", Journal of Biological Chemistry, May 10, 1971, vol. 246, No. 9, pp. 2734-2744.

Bourdillon, Christian, et al, "A Fully Active Monolayer Enzyme Electrode Derivatized by Antigen-Antibody Attachment", Journal of the American Chemical Society, 1993, vol. 115, No. 26, pp. 12264-12269.

Forster, Robert J., "Electron Transfer Dynamics and Surface Coverages of Binary Anthraquinone Monolayers on Mercury Microelectrodes", Langmuir, 1995, vol. 11, No. 6, pp. 2247-2255.

Forster, Robert J. et al, "Kinetic Separation of Faradaic Currents: Binary Monolayers as Model Systems", Analytical Chemistry, Apr. 1, 1995, vol. 67, No. 7, pp. 1232-1239.

\* cited by examiner

CUSTOMIZABLE AND RENEWABLE NANOSTRUCTURED INTERFACE FOR BIOELECTRONIC APPLICATIONS

CROSS-REFERENCE TO RELATED APPLICATIONS

This application claims the benefit of U.S. Provisional Patent Application No. 60/679,922, filed May 10, 2005, entitled CUSTOMIZABLE AND RENEWABLE NANOSTRUCTURED INTERFACE FOR BIOELECTRONIC APPLICATIONS, the entire contents of which are incorporated by reference.

FIELD OF THE INVENTION

This invention relates to the field of bionics, also known as biomimetics, and more particularly to bioelectronic devices (biomimetic sensors, biomedical devices, catalytic systems, etc.) and chemical structures useful for preparing biomimetic devices.

BACKGROUND OF THE INVENTION

Efficient electrical contacting of redox-enzymes with electrodes is a key process in the tailoring of enzyme-electrodes for bioelectric applications such as biosensors. As redox-enzymes usually lack direct electrical communication with electrodes, therefore previously many approaches involving the application of diffusional electron mediators, the tethering of redox-relay groups to the protein, or the immobilization of the enzymes in redox-active polymers have been used to establish electrical communication between the redox-proteins and the electrodes. However, relatively inefficient electrical contacting was achieved in these approaches due to the nonoptimal modification of the enzymes by the redox-tethers, or the lack of appropriate alignment of the enzymes with respect to the electrode. Very efficient electrical coupling can be achieved if the enzyme, its cofactor, and the electron mediator are in proper orientation at the electrode. Recently, efficient electrical communication between redox-proteins and electrodes was achieved by the reconstitution of apo-enzymes on relay-cofactor monolayers associated with electrodes.

Dehydrogenases enzymes essential for cellular metabolism are often used as a biocatalyst for chiral chemicals or for sensing applications due to enzymes activity, thermal stability, ability to function in the presence of molecular oxygen. Secondary 30 alcohol dehydrogenases (2° ADH's) are a class of enzymes, using nicotinamide adenine dinucleotide, NAD+, (EC 1.1.1.1), nicotinamide adenine dinucleotide phosphate, NADP+(EC 1.1.1.2), or both (EC 1.1.1.71) as the cofactor. Many dehydrogenase enzymes require the diffusion of the cofactor into the Rossmann fold of the protein. This process allows electrons to be freely transferred between the redox-center of the protein and the cofactor. However, the difficulties associated with in situ regeneration of the enzyme's cofactor have hindered commercial development of dehydrogenasebased biosensors and biocatalytic reactors. Both the direct electrochemical oxidation 5 and reduction of NAD(P)+are kinetically unfavored, requiring the use of high overpotentials. The potential needed for direct oxidation (approximately IV vs Standard Calomel electrode (SCE)) is subject to interference of ascorbic acid and molecular oxygen. The potential needed for oxidation and reduction of NAD(P)+, can be reduced with the use of electron mediators which transfers electrons between the electrode and 10 the cofactor at more moderate voltages (−0.15 to 0.15 V). Suitable mediators include quinones, ferrocenes, phenylendiimines, phenoxazines, toluidine blue (TBO), phenothiazines, catechols, metal complexes, and organic conducting salts. However, there are some fundamental problems with the use of a diffusional electron mediators for electrochemical detection. Many electron mediators such as Meldola's Blue (MB) and 15 toluidine blue (TBO) are known to electropolymerize on the electrode. To overcome this problem electron mediators have been electrochemically tethered to the protein, the electrode, or immobilized in a polymer matrix.

Electrodes have previously been coated with a thin layer of conductive polymers (polypyrrole (PPy) and polyanaline (PA)); these electrodes have been shown to accelerate the oxidation of NADH. Poly(thionine), poly(3,4-di-hydroxybenzaldehyde), poly(metallophthalocyanine), poly(o-aminiophnol)(PAP) and poly(ophenylenediamine) have shown the ability to mediate electron transfer and have been reported to easily form polymer matrices. Polypyrrole (PPy) and PA, along with other conductive polymers which have shown to transfer electrons, are known to change morphology. Other approaches include the incorporation of the electron mediators or cofactors into the polymer matrixes either by physical encapsulation or by covalent modification. Polyelectrolytes, e.g. polyacrylic acid (PAA) and poly(allylamine) hydrochloride (PAH), can be assembled on the surface, while the surface morphology of the polyelectrolyte on the electrode by manipulating the degree of protonation. PAH and PAA can be adsorbed onto any negatively or positively, respectively, charged electrode. The reactive end groups of the polyelectrolytes allow for the fabrication of an electron transfer scaffold.

Several approaches have been developed to facilitate electron transfer between the electrode and enzyme, including the use of a diffusional mediators to shuttle electrons between the electrode and cofactor, immobilizing the enzymes in conductive polymers, and constructing redox relays by attaching enzymatic cofactors inside imprinted polymers. Many enzyme-immobilization methods result in the random orientation of the redox centers of the proteins relative to the electrode. Ideally, interfaces should maintain the mediator, the cofactor, and the enzyme in a proper orientation, prevent degradation and diffusional loss of components, be customizable to adapt to different mediators, cofactors, and enzymes, as well as be inexpensive to fabricate. Zayats et al. assembled on the electrode a linear molecular chain consisting of the mediator, the cofactor and the enzymes, maintaining each of the components in the proper spatial orientation. This approach has been shown to work with flavoenzymes, hemoproteins, as well as pyrrolquinoline quinine (PQQ) containing enzymes. The cofactor, $NAD(P)^+$, was bound to the electrode through a phenylboronic acid affinity linkage with cis-diol functionality of the cofactor. The use of a boronic acid affinity linkage allows the enzyme to bind to the cofactor, allowing efficient, multistep electron transfer, and prevented component losses due to diffusion. However, this approach has the disadvantage of requiring two linkages to be formed with the electron mediator: one with the electrode, and the other with the cofactor.

SUMMARY OF THE INVENTION

The present invention provides improved biomimetic devices and chemical structures useful for preparing bioelectronic devices, in which biologically active compounds, such as enzymes, are bound, either directly or indirectly, to a polyelectrolyte, which may be reversibly bound to a treated substrate electrode to facilitate regeneration of the electrode by removal of the polyelectrolyte and biologically active compound, and reapplication of a new electrolyte and new biologically active compound. Because the polyelectrolyte is electrostatically bound to the treated electrode substrate, removal is easily facilitated by changing conditions, such as pH. This allows the most expensive part (the electrically conductive substrate) of a biomimetic device or array of biomimetic devices to be easily regenerated at a reasonable cost, thereby facilitating such applications as rapid, low cost bioassays.

These and other features, advantages and objects of the present invention will be further understood and appreciated by those skilled in the art by reference to the following specification, claims and appended drawings.

DETAILED DESCRIPTION OF PREFERRED EMBODIMENT

Figure 1:
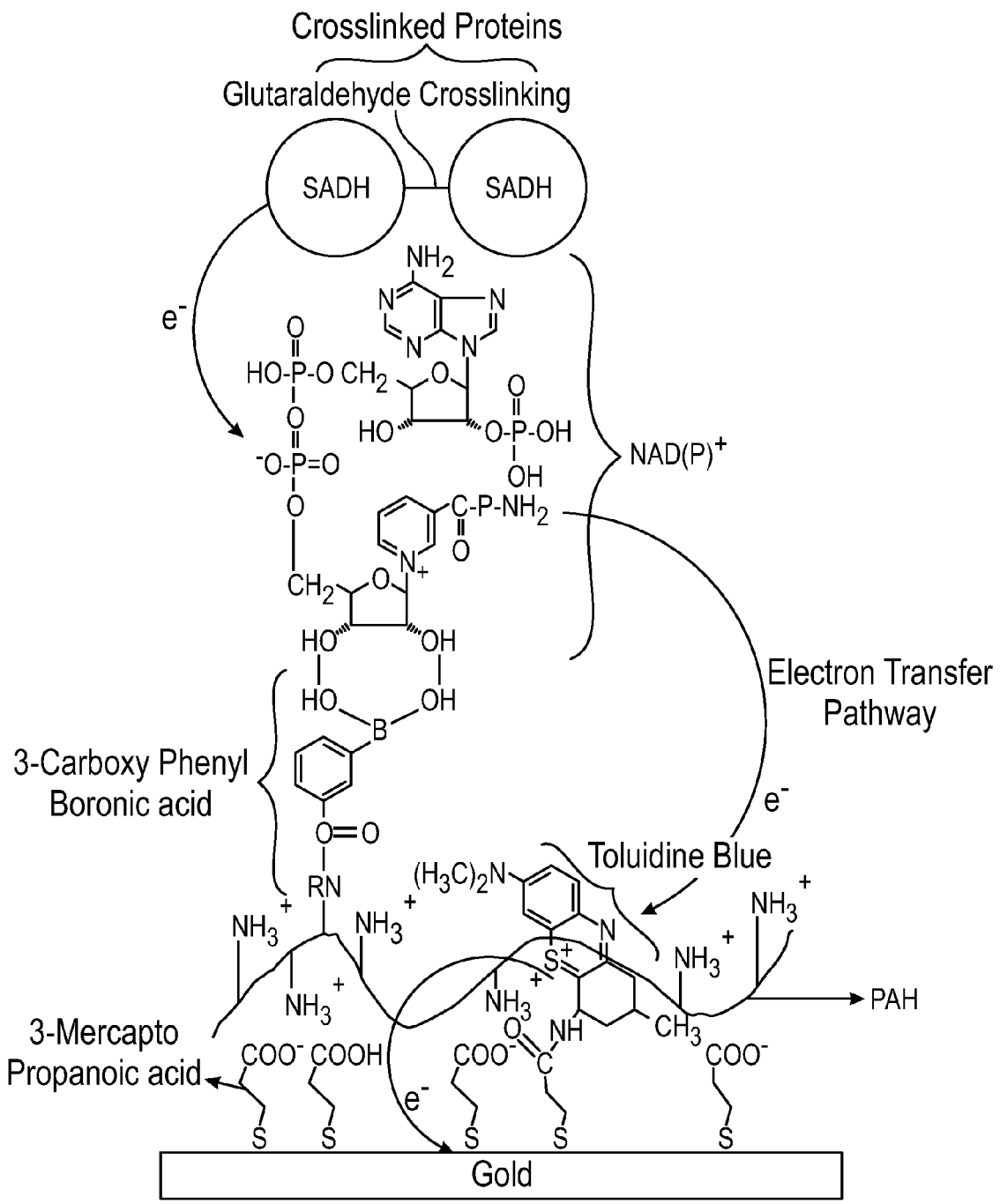
FIG. 1 is a schematic illustrating the electron transfer mechanism for a biomimetic sensing device in accordance with the invention.

Previously, solutes were pre-loaded into the hydrophilic layer when the lipid membrane is produced. In this approach, no allowance is made for solute replenishment as the solutes are depleted. In contrast, the present application discloses a way to allow replenishment by providing mechanisms of solute transport across the lipid membrane to/from the reservoir. According to one aspect of the present invention, lipid-walled reservoirs (liposomes, endosomes, granules, etc.) can be used to transfer solutes across the lipid membrane in several ways. For example, liposomes can be fused with the membrane, transferring the liposomes' contents. Also, membrane proteins can achieve transmembrane solute exchange while keeping the lipid-walled reservoirs intact. The present invention has substantial utility in development of biosensors and methods to screen drug candidates. It permits functional biomimetic interfaces containing lipid membranes, such as lipid bilayers, to be regenerated as solutes are depleted from the hydrophilic layer underlying the lipid membrane, thus extending the useful lifetimes.

Biomimetic interfaces consisting of synthetic lipid membranes allow proteins to be immobilized in an active conformation on a surface. For example, deposition of a biomimetic interface on an electrode allows transduction of the protein's activity into an electrical signal, thus yielding a biosensor. Such systems have applications in protein-based electrochemical biosensors that could detect a variety of chemical and biological analytes. Biomimetic interfaces consisting of a lipid membrane separated from the working electrode by a hydrophilic layer are disclosed. These biomimetic interfaces have been integrated into a fully scalable, three-electrode system on a silicon chip, The resulting integrated biosensor can be readily miniaturized to produce high-density, multianalyte arrays.

In many cases, activity of the biomimetic interface requires the presence of water-soluble solutes in the hydrophilic layer between the lipid membrane and the underlying surface (e.g., electrode). Such solutes can be depleted by reaction, diffusional loss, or degradation, causing the interface to lose its activity. The present invention provides a mechanism to transfer hydrophilic solutes across the lipid membrane. Spent solutes can be removed from the reservoir, and fresh solutes can be added to the reservoir, thus extending the useful lifetime of the biomimetic interface.

The present invention provides an improved method to interface dehydrogenase enzymes to electrodes. It allows the electrode to exchange electrons with the enzymes through intermediate electron-carrying molecules known as the mediator (e.g., toluidine blue O) and the cofactor (e.g., NAD $(P)^+$). The molecules are chemically bonded to charged polyelectrolytes (e.g., poly(allylamine) hydrochloride), which allow efficient electron transfer, prevent diffusional loss of the mediator and cofactor, and allow the interface to be conveniently installed on, and removed from, the electrode.

The present invention simplifies the process of installing the bioelectronic interface and provides a convenient means to remove the interface. In this way, the interface can be readily regenerated. This feature provides substantial advantages because the enzyme and cofactor have finite lifetimes, while the biosensor hardware lasts indefinitely. The ability to regenerate the electrode greatly reduces the cost of use by allowing the biosensor hardware to be reused. However, this approach makes interface regeneration practical for extremely thin (nanostructured), high-performance biosensor interfaces.

The present invention provides the following desirable features. The enzyme, electron mediator and the cofactor are coupled in such a way to (1) prevent diffusional loss of the enzyme, (2) control the spatial orientation of the cofactor and enzyme to achieve efficient electron transfer, (3) require only a single chemical bond formed by the electron mediator, and (4) allow bioelectronic interfaces based on $NAD(P)^+$ dependent dehydrogenase enzymes to be used, and (5) allow convenient installation, removal, and replacement on the electrode. The use of weak polyelectrolytes allow for the electrodes to be renewed as well as the ability to customize the nanostructured bioelectric interface. The use of poly(ethyleneimine) (PEI) allows the formation of electrodes using different enzymes each time the electrode is regenerated.

Carboxylic acid terminated thiol is reacted to the electrode surface which is reacted with the electron mediator. The charged polyelectrolytes are electrostatically attracted to the chemically modified electrode. The positively charged polyelectrolytes are modified with 3-carboxyphenyl boronic acid, which is used to chemically modify the polyelectrolyte to incorporate the enzymatic co-factor and enzyme.

Examples of several fully functional biosensors according to the present invention are disclosed. In two embodiments, 3-mercaptopropanoic acid, toluidine blue O, PAH (or PEI), and $NAD(P)^+$ were used to make biosensors for iospropanol using $NADP^+$-dependent secondary alcohol dehydrogenase and for sorbitol using $NAD^+$-dependent-sorbitol dehydrogenase.

The preparation of a polyelectrolyte based enzyme electrode which contains an integrated and electrically active $NAD(P)^+$ dependent enzyme is described. A major challenge in the formation of such bioelectronic interfaces is assembling the enzyme, its cofactor, and an electron mediator in proper orientation so that efficient electron transfer is achieved. This paper describes a new approach for efficient electrical contacting between dehydrogenase enzymes and electrodes by coupling secondary alcohol dehydrogenase (2° ADH) with a polyelectrolyte. This unique macromolecular approach provides greater flexibility in assembling complex bioelectronic interfaces than the two-dimensional cross linking of proteins to the surface and the rigid-linear approaches for the attachment of the electron mediator, cofactor, and the enzyme. In this new approach, 3-mercaptopropanoic acid (MPA) was self-assembled on a gold electrode and then the electron mediator toluidine blue O (TBO) was reacted with MPA's carboxyl group via an amide bond. Poly(allylamine hydrochloride) (PAH) was then electrostatically adsorbed onto the MPA layer via electrostatic interactions. β-nicotinamide adenine dinucleotide $(NAD(P)^+)$ was then reacted with primary amines on PAH using a boronic acid linkage. Secondary alcohol dehydrogenase (2° ADH) was then absorbed on this interface to yield an isopropyl alcohol biosensor that showed linear response up to 40 mM. A $NAD^+$ dependent mutant of 2° ADH was also used for electrochemical studies. Various parameters such as pH, temperature and concentration were used to optimize the long and short-term stability and calibration of the resulting bioelectronic interfaces. The 2° ADH enzyme-electrode (surface coverage $2.0 \times 10^{-12}$ mol $cm^{-2}$) exhibited a turnover rate of 152 $s^1$. Cyclic voltammetry was used to confirm electrical communication between the redox centers of the enzymes, the electron mediator and the electrodes. Fluorescence microscopy, quartz crystal microbalance and microcontact printing were used to characterize the electrode and check the feasibility of the proposed approach. The resulting interface system has potential applications in the development of a new class of biosensors, catalytic systems, and biomedical devices.

The preparation of a polyelectrolyte based renewable enzyme electrode which provides efficient electrical coupling between the enzyme, its cofactor, an electron mediator and the electrode is described. In this new approach 3-mercaptopropanoic acid (MPA) was self-assembled on a gold electrode and the electron mediator toluidine blue O (TEO) was reacted with MPA's carboxyl group via an amide bond. Poly(ethylene imine) (PEI) was then electrostatically adsorbed onto the MPA layer via electrostatic interactions. The primary amines on PBI were then used to attach P-nicotinamide adenine dinucleotide phosphate $(NAD(P)^+)$ using a boronic acid linkage. Secondary alcohol dehydrogenase (sADH) was then absorbed on this interface to yield an isopropyl alcohol biosensor that showed linear response up to 40 mM. The response of this sensor is stable at normal pH range (pH 7-8). However, on washing with low pH solution, the current response of this sensor to different isopropanol concentrations returns nearly to the background value due to the removal of adsorbed layers. But, the current response returns nearly to the original value on subjecting the electrode again to another assembly cycle. These results suggest the isopropanol sensor made using this self-assembly can be used repeatedly. Cyclic voltammetry, fluorescence microscopy, quartz crystal microbalance, microcontact printing and atomic force microscopy were used to characterize the electrode and check the feasibility of the proposed approach. Potential applications of these interfaces include biosensors, catalytic systems and biomedical devices.

Efficient electrical contacting of redox-enzymes with electrodes is a key process in the tailoring of enzyme-electrodes for bioelectronics applications such as biosensors. As redox-enzymes usually lack direct electrical communication with electrodes, therefore previously many approaches involving the application of diffusional electron mediators, the tethering of redox-relay groups to the protein, or the immobilization of the enzymes in redox-active polymers have been used to establish electrical communication between the redox-proteins and the electrodes. However, relatively inefficient electrical contacting was achieved in these approaches due to the non-optimal modification of the enzymes by the redox-tethers, or the lack of inappropriate alignment of the enzymes with respect to the electrode. Very efficient electrical coupling can be achieved if the enzyme, its cofactor, and an electron mediator are in proper orientation at the electrode. Recently, efficient electrical communication between redox-proteins and electrodes was achieved by the reconstitution of apo-enzymes on relay-cofactor monolayers associated with electrodes.

The use of organic films in integrated optics, microelectronic devices, sensors, and optical memory devices require a means of patterning and controlling the device architecture. Microcontact printing (gCP) provides a versatile method for chemically and molecularly patterning surfaces. This technique is attractive due to its high fidelity and .me of duplication. gCP uses a stamp which contains the desired molecule; the molecules residing on the raised regions of the stamp are brought in contact with the substrate when the stamp is printed. The transfer efficiency of the molecules from the stamp to the substrate depends on the relative strength of interaction of the molecules with the substrate versus the stamp. The ionic Layer-by-layer (LBL) assembly technique, introduced by Decher in 1991, formed films by electrostatic interactions between oppositely charged poly-ion species to create alternating layers of absorbed poly-ions. "{Polyclectrolyte multilayers" (PEMs) are an effective and economical approach for the deposition of ultrathin organized films and have been modified to incorporate organic dyes, colloids, and inorganic nanoparticles. Tn order to establish electrical communication electrically conductive polymers, polypyrrole (PPy) and polyananline (PA), are used to accelerate the oxidation of NADH. Other approaches include the incorporation of the electron mediators or cofactors into the polymer matrixes either by physical encapsulation or by covalent modification. Polymer films displaying mediating abilities include: poly(thionine),-poly(3,4-dihydroxybenzaldehyde, poly(metallophthalooyanine), poly(o-aminiophnol)(PAP) and poly(o-phenylenediamine).

The development of a generic bioelectronic interfaces, which provide mediated electron transfer to a wide variety of dehydrogenase enzymes, facilitate the commercial applications of these enzymes. Such interfaces should exhibit the following properties: (1) maintain the mediator, the cofactor, and the enzyme in a proper orientation relative to the electrode for rapid and efficient electron transfer; (2) prevent degradation and diffusional loss of components for long operational lifetimes; (3) be customizable to adapt to different mediators, cofactors, and enzymes; (4) be inexpensive to fabricate.

Covalent linkages have been used to facilitate rigid linear electron-transfer scaffold including the electrode; the mediator, and the cofactor. Affinity binding between the cofactor and enzyme complete the chain. The covalent and affinity linkages used in this arrangement provide efficient electron transfer and prevented losses due to diffusion. However, this approach requires the electron mediator to form two linkages: one with the electrode, and the other with the cofactor. Recently, an electron transfer scaffold was developed using a to -functional linking molecule (cysteine). The new mechanism facilitates electron transfer, with out the use of a bi-functional co-factor, where one branch reacts with the enzymes cofactor, while the other branch reacts with the electron mediator.

Dehydrogenase enzymes form a vast class of NAD(P)$^}$INAD(P)H dependent redox enzymes, which are ideally suited for use in bioelectronic applications, due to their ability to function in the absence of molecular oxygen. However, there are some fundamental difficulties including electrical contacting of the proteins with the electrodes, due to the diffusional nature of the cofactors. The catalytic activity of these enzymes involves the diffusion of NAD(P)$^}$/NAD(P)H cofactors into the proteins, the formation of temporary conglomerates that enable electron transfer between the redox center and the cofactor, and the subsequent diffusion of the reduced (or oxidized) cofactor from the protein. For bioelectronic applications, the integrated enzyme electrode should lack diffusional components. Also, the diffusional steps can be rate limiting therefore it is desirable to minimize the number of diffusional components. This can be achieved by covalently binding the cofactor units to the electrode.

Furthermore, NAD(P)$^+$/NAD(P)H cofactors inefficient at exchanging electrons with metal electrodes. The direct electrochemical oxidation of NAD(P)H or the direct reduction of NAD(P) is kinetically unfavored, requiring the use of high overpotentials. The NAD$^+$ radicals generated in the electrochemical oxidation of NAD(P) can dimerize or polymerize, resulting in the degradation of cofactors. In addition, biosensors operated at the potential needed for direct oxidation of the NAD(P)H, are subject to interference due to compounds such as ascorbic acid. This problem can be alleviated by the use of electron mediators to shuttle electrons between the electrode and the cofactor, allowing the NAD(P)H to be oxidized at more moderate voltages (−0.15 to 0.15 V), within which common interfering compounds are neither oxidized nor reduced. Suitable mediators include quinones, ferrocenes, phenylendiimines, phenoxazines, toluide blue (TBO), phenothiazines, catechols, metal complexes, and organic conducting salts.

Previous reports addresses the generation of enzyme modified electrodes: through the formation of a linear or branched electron transfer scaffolds, where the enzyme along with its cofactors and associated electron mediator are covalently bound to the electrode. The chemical attachment of the enzymes, secondary alcohol dehydrogenase, to polyelectrolyetes such as PAH, has also been shown. The present study describes a novel approach that can improve upon the limitations of previous approaches and allows bioelectronic interfaces to be removed and refabricated. The current method electrically contacts NAD(P)$^+$ dependent enzymes to gold electrodes by using poly(ethyleneimine) (PEI) as a building block for the electron transfer scaffold. The protonated amine groups can be electrostatically bound to negatively charged surfaces. By varying the salt concentration and pH provides controls the degree of binding and conformation of PEI on the surface. Cyclic voltammetry and chronoamperometry were used to establish electrical communication between the enzyme and the electrode. Fluorescence microscopy, quartz crystal microbalance, and atomic force microscopy were used to confirm assembly. We capitalized upon ionic interactions to deposit a thin film, uniform PEI self-assembled monolayer patterns across the top of mercaptoproanoic acid films, using microcontact printing.

In accordance with certain aspects of this invention, bioelectric devices, such as bioelectric sensors, are comprised of a chemically modified electrically conductive substrate, a polyelectrolyte electrostatically bound to the chemically modified electrically conductive substrate, and a biologically active compound bound, directed or indirectly to the polyelectrolyte. Binding of the biologically active compound to the polyelectrolyte may encompass any of a variety of mechanisms, including covalent bonding, ionic bonding, electrostatic attraction, hydrogen bonding, London dispersion forces, etc. In this sense, it is only necessary that the binding of the biologically active compound to the polyelectrolyte be of sufficient strength to prevent migration of the biologically active compound during use of the biomimetic device, such that the biologically active compound is in appropriate proximity to the electrically conductive substrate and any mediators or cofactors incorporated into the biomimetic device. The electrically conductive substrate may be comprised of any material suitable for preparing an electrode, such as gold, silver, copper, platinum, doped silica or glass semiconductors, etc. Chemical treatment of the electrically conductive substrate involves binding chemical compounds or moieties to the surface of the substrate which have free terminal ionic or ionizable species, such as carboxyl groups, quaternary ammonium groups, etc., that can be used for electrostatically binding the polyelectrolyte to the chemically modified substrate. Suitable polyelectrolytes include both polyanions and polycations. Examples of polyanions includes poly(acrylic acid), poly(aspartic acid), poly(glutamic acid), poly(vinyl acetate), and salts thereof. Poly(cations) include poly(acrylamide-co-diallyldimethylammonium), poly(allylamine), poly(L-lysine), poly(histidine), poly(ethyleneimine) (either linear or branch), and poly(arginine), and salts thereof. Examples of biologically active compounds that may be incorporated into the biomimetic device of this invention include various enzymes, such as dehydrogenase. Typically, in the case of dehydrogenases, enzymatic cofactors are required to achieve activity of the enzyme. In such case, the enzymatic cofactor may be chemically bound, either directly or indirectly, or through a linking group, to the substrate or to the polyelectrolyte, and the biologically active compound or enzyme may be bound to the cofactor via the normal interactions between an enzyme and its cofactor. In some cases, in order to supplement binding of the enzyme to its cofactor and/or to prevent migration of the enzyme, the enzymes may be chemically cross-linked to each other.

As mentioned earlier, it is often desirable to provide an electron carrying compound or mediator to reduce the electrical potential needed to transfer electrons between the electrode and the cofactor. Electron-transfer mediators are synthetic or biologically-active charge-carriers that transfer electrons between a redox-enzyme and an electrode. In generally, in order to maintain the electron-transfer mediators in suitable proximity to the cofactors and the electrically conductive substrate, the enzyme cofactor is chemically bonded to the substrate or the polyelectrolyte. Because of the reaction kinetics, it is possible to control the extent to which the mediator is chemically bonded to the substrate or the polyelectrolyte to provide adequate residual reactive sites for bonding an enzyme, an enzymatic cofactor and/or other biologically active compound to the remaining reactive sites of the substrate and/or the polyelectrolyte.

It is also envisioned that a chemical composite comprising a polyelectrolyte having a biologically active compound bound, directly or indirectly, to the polyelectrolyte, and/or an enzyme cofactor bound to the polyelectrolyte, either directly or indirectly, and optionally having a mediator chemically bounded to the polyelectrolyte, could be prepared (e.g., such as in a solution) and used for regenerating the biomimetic devices of this invention, such as after spent biologically active compound, polyelectrolyte and optional mediators and/or cofactors are stripped from the electrically conductive substrate.

Particular aspects of the invention will be described in further detail in the following examples, which are illustrative, but not limiting of the invention.

EXPERIMENTAL SECTION 1

Chemicals:

Fluoroscein isothiocyanate (FITC) was purchased from Molecular Probes (Eugene, Oreg.). The cofactors of 2° ADH, β-nicotinamide adenine dinucleotide ($NAD^+$) respectively, were purchased from Sigma. All other chemicals, including poly(diallyldimethylammonium chloride) (PDAC) ($M_w$~100,000-200,000) as a 20 wt % solution, 3-mercaptopropionic acid (MPA), toluidine blue O (TBO), nile blue A (NBA), 3-carboxyphenyl boronic acid (CBA), 1-ethyl-3-(3-dimethylaminopropyl)carbodiimide (EDC), N-hydroxysuccinimide (NHS), glutaric dialdehyde (25% in water), ethanol, 2-propanol, sodium phosphate monobasic, sodium phosphate dibasic, dimethyl sulfoxide (DMSO), poly(allyamine hydrochloride) (PAH), and sodium bicarbonate, were obtained from Sigma and Aldrich. Tryptone and yeast extract were purchased from Fisher Scientific. Poly-(dimethylsiloxane) (PDMS) from the Sylgard 184 silicone elastomer kit (Dow Corning, Midland, Mich.) was used to prepare stamps. Ultrapure water (18.2 MΩ) was supplied by a Barnstead Nanopure-UV four-stage purifier equipped with a UV source and a 0.2 μm filter (Barnstead International Dubuque, Iowa).

Media and Strains:

*Escherichia coli* (DH5α) containing the wild-type and G198C 2° alcohol dehydrogenase from *Thermoanaerobacter ethanolicus* (2° ADH) recombinant plasmids were grown in rich complex media (20 g/L tryptone, 10 g/L yeast extract, 5 g/L NaCl) at 37C in the presence of 25 μg/mL kanamycin and 100 μg/mL ampicillin[40,41]. The recombinant enzyme was purified using the protocol outlined by Burdette; however the pelleted cells were lysed using a power laboratories french press instead of using liquid nitrogen.

Fluorescent Labeling of Protein:

A 5.5 mg sample of 2° ADH, in 2 mL Tris buffer, pH=5.8, was dialyzed against a 1 M sodium bicarbonate solution, pH=9, for 24 h. The bicarbonate solution was changed every 6 h during the dialysis process. 100 μL of dimethyl sulfoxide (DMSO) was combined with 0.05 mg FITC. The DMSO-FITC solution was then added to the protein solution, and continuously stirred in the dark for 2 h. The protein was then dialyzed against deionized water for 24 h, changing the water every 6 h, to remove excess FITC.

Electrode Modifications:

Gold electrodes (1 cm by 0.5 cm rectangular electrodes, roughness factor 1.2) were used for modifications. The electrodes were boiled in piranha solution, 70% sulfuric acid-30% hydrogen peroxide, for 1 min, followed by rinsing the electrode with water. The electrodes were stored in concentrated sulfuric acid. Prior to modification, the electrodes were rinsed thoroughly with water, soaked for 10 min in concentrated nitric acid, rinsed with water, and dried under nitrogen. A cyclic voltammogram was recorded in 1 M $H_2SO_4$ to evaluate surface cleanliness prior to modification. The gold electrodes were then soaked in a 0.05 M solution of 3-meraptopropanoic acid (MPA) in ethanol for 2 h and then rinsed with ethanol to remove the physically absorbed MPA. The MPA modified gold electrodes were reacted for 2 h in a 1 mM solution of toluidine blue (TBO) in 0.1 M phosphate buffer (PBS), pH=7.4, in the presence of 10 mM NHS and 5 mM EDC. A poly(allyamine) hydrochloride (PAH) monolayer was adsorbed onto the TBO-functionalized electrode by immersing the electrodes in a 10 mM PAH aqueous solution for 2 h. The electrodes were then rinsed to remove the weakly adsorbed material. The gold electrodes functionalized with PAH were then reacted with a 1 mM 3-carboxyphenyl boronic acid (CBA) solution in 0.1 M PBS, pH=7.4, in the presence of 5 mM EDC and 10 mM NHS for 2 h. The gold electrodes functionalized with TBO and CBA were further functionalized with the enzymatic cofactors, $NADP^+$ or $NAD^+$. The CBA functionalized gold electrodes were then reacted with a 5 mM solution of the respective cofactor in phosphate buffer, pH=7.4, for 2 h, and washed with water. The $TBO-NADP^+$ and $TBO-NAD^+$ functionalized gold electrodes were then reacted with 4.4 mg $mL^{-1}$ 2° ADH and 5.7 mg $mL^{-1}$ G198D 2° ADH respectively, in phosphate buffer, pH=7.4, for 2 h at room temperature. The electrodes were then washed with water and reacted with 25% (v/v) glutaric dialdehyde in water for 20 min. The electrodes were then washed with water and used for the bio-catalytic oxidation of 2-propanol.

Preparation of PDMS Stamp:

An elastomeric stamp is made by curing poly(dimethylsiloxane) (PDMS) on a microfabricated silicon master, which acts as a mold, to allow the surface topology of the stamp to form a negative replica of the master, The PDMS stamps were made by pouring a 10:1 solution of elasatomer and initiator over a prepared silicon master[42]. The silicon master was pretreated with fluorosilanes to facilitate the removal of the PDMS stamps from the silicon masters. The mixture was cured overnight at 60° C. The masters were prepared in the Microsystems Technology Lab at MIT and consisted of features (parallel lines and circles) from 1 to 10 μm.

Stamping 3-Mercaptopropanoic Acid:

The 1 mM 3-mercaptopropanoic acid ink was made with ethanol as the solvent. After solvent evaporation the PDMS stamp was dried under nitrogen and brought into contact with the substrate for 1 min at room temperature. Cotton swap inking was used to ink the PDMS stamp. The cotton swap was soaked in the ink and rubbed over the surface of the stamp, the stamp was then dried under nitrogen. Following the stamping process, the patterned surface was thoroughly rinsed with ethanol to remove the unbounded molecules to prepare a patterned uniform monolayer. The MPA was stamped on a gold electrode followed by the sequential deposition process, described earlier, to build the electrode process in the area in which the MPA was stamped.

Characterization:

Electrochemical Techniques

A conventional three-electrode system consisting of the enzyme-modified gold working electrode, a platinum auxiliary electrode, and a saturated silver/silver chloride (Ag/AgCl) reference electrode isolated by a glass frit, were used for the electrochemical measurements. All potentials are reporated against the saturated Ag/AgCl reference electrodes. The electrochemical cell was placed into a grounded Faraday cage (Bioanalytical Systems, BAS, West Lafayette, Ind., C-3 cell stand). Cyclic voltammetry and chronoamperometry were performed using an electrochemical analyzer composed of a potentiostat/galvanostat (BAS CV-50W) connected to a computer (BAS CV-50W Version 2.3).

Microgravimetric Measurements

Microgravimetric measurements were used to monitor the assembly of the enzyme electrode. A quartz crystal microbalance (QCM) analyzer (Maxtek, Research Quartz Crystal Microbalance, Santa Fe Springs, Calif.) linked to a computer running RQCM® data logging software was used for the microgravimetric measurements. Quartz crystals (AT-cut, 5 MHz) sandwiched between two gold-electrodes (geometric area 1.25 cm$^2$, roughness factor approximately 0.9) were used. The electrode surfaces were washed with ethanol and modified as described above for the gold electrodes. Frequency changes of the quartz crystals were measured in 10 mM HEPES buffer, pH=7.0, to track changes of mass during each step of the interface assembly. All measurements were carried out at room temperature (25.0±2° C.). Masses of individual layers deposited were calculated from QCM measurements using the Sauerbrey equation, Eq 1, in which the frequency change, $\Delta F$, is linearly related to the mass change ($\Delta M$) on the quartz crystal[43], $$\Delta F = \frac{-2 f_0^2 \Delta M}{A \sqrt{\mu \rho}}$$

where $f_0$ is the fundamental resonance frequency of the quartz crystals (5 MHz), $\mu$ is the shear modulus of the quartz (2.94× 10$^1$ g cm$^{-1}$ s$^{-2}$), $\rho$ is the density of the crystal (2.648 g cm$^{-3}$(, and A is the projected surface area of the electrode (1.26 cm$^2$). For this system, a decrease in frequency of 1 Hz corresponds to a mass increase of 17.6 ng cm$^{-2}$, provided the frequency shift can be ascribed exclusively to mass effects and not to changes in solution density or viscosity. The molar surface coverage, $\Gamma$ (mol/cm$^2$), of the monolayer was calculated using Eq 2, where $M_w$ is the molecular weight. Combining Eq 1 and Eq 2, you could determine the surface coverage as a function of the measured frequency shift, Eq. 3.

$$\Gamma = \frac{\Delta M}{\Delta M_w}$$

$$\frac{\Delta M}{\Delta M_w} = (\Gamma) = \frac{\Delta F \sqrt{\mu \rho}}{2 M_w f_0^2}$$

For this system, a decrease of 1 Hz corresponds to a surface coverage of 3.5×10$^{-12}$ mol cm$^{-2}$, provided the frequency shift can be ascribed exclusively to mass effects.

Fluorescent Microscopy

Flurescence images were obtained using a Nikon Eclipse E 400 microscope (Nikon, Melville, N.Y.). The resulting patterned TBO-PAH-NAD(P)$^+$ electrodes were dipped in the fluorescently labeled 2° ADH solutions for 1 hr and then viewed under the fluorescence microscope.

Results and Discussion:

Microgravimetric Measurements

Figure 2A:
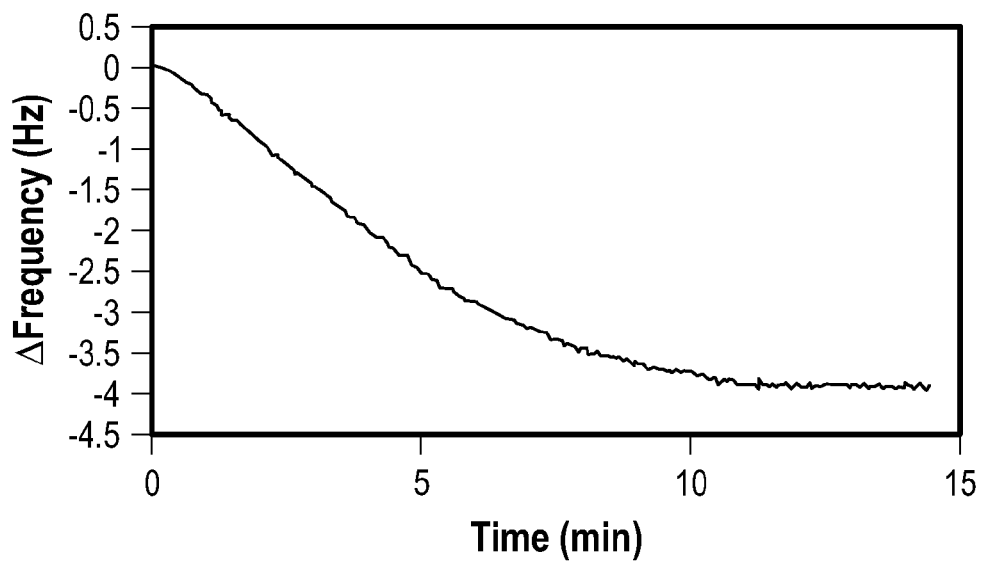
FIG. 2A-2C are quartz crystal microbalance (QCM) measurements of toluidine blue O (TBO) in the presence of 5 mM EDC,(b) 10 mM, poly(allyamine)hydrochloride (PAH) and (c) NADP+ in 10 mM AGPES buffer (pH=7.0) on a 3-mercaptopropanoic acid treated gold surface after ENC/NHS activation.
Figure 2B:
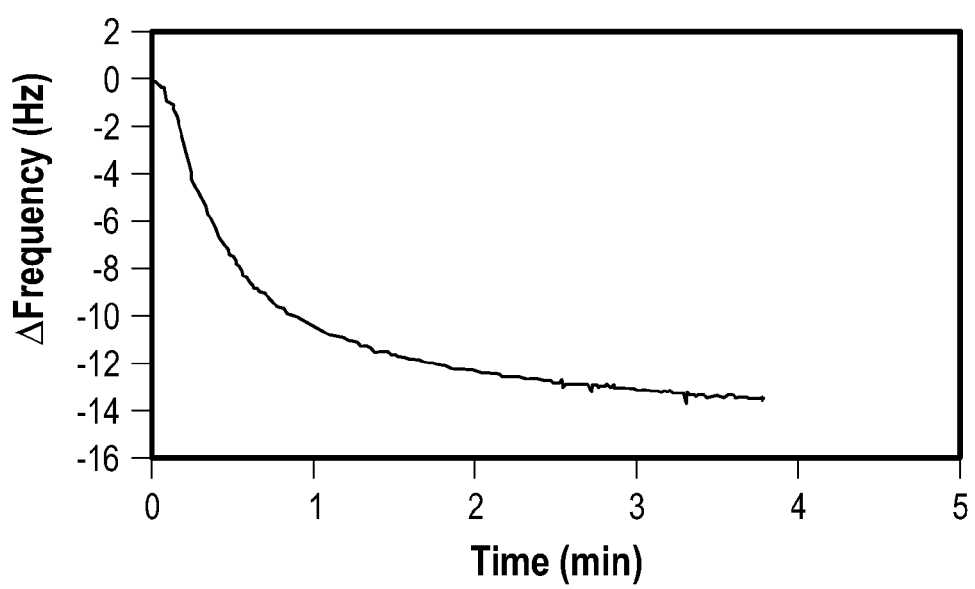
Figure 2C:
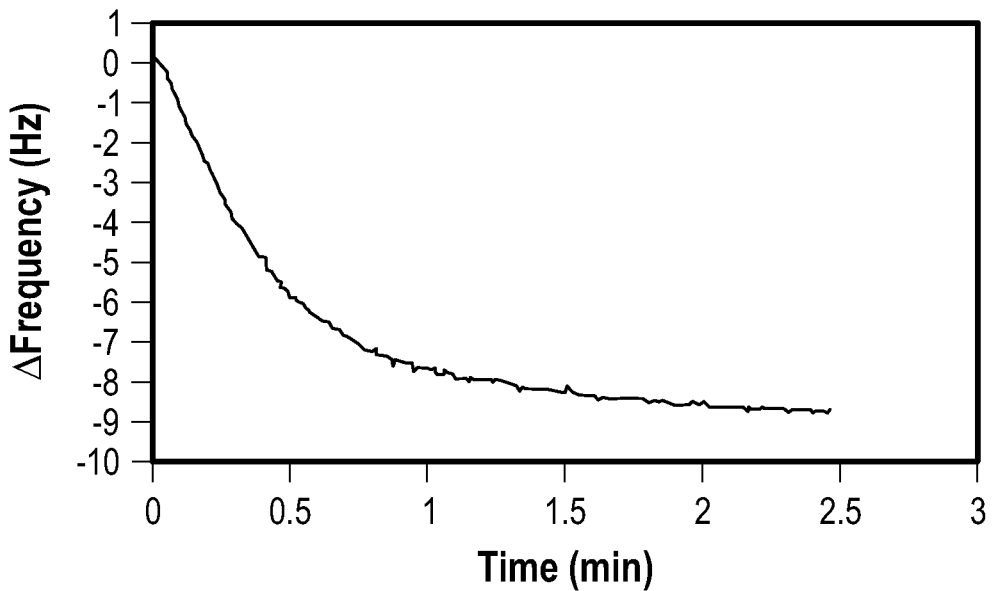

Quartz-crystal microbalance, QCM analyses were performed on the stepwise formation of the bioelectronic interface on a gold-quartz crystal. FIG. 2A-2C depict the frequency changes corresponding to the addition of (a) 10 mM TBO (in the presence of 5 mM EDC), (b) 10 mM PAH, and (c) 5 mM NAD(P)+, respectively. The average frequency change was −5.5 Hz, −13 Hz, and −9Hz, for the addition of TBO, PAH, and NAD(P)$^+$ respectively. The measured frequencies correspond to a surface coverage of 3.1×10$^{-10}$ and 2.8×10$^{-10}$ mol cm$^{-2}$ respectively for TBO, and NAD(P)+; the surface coverage of the PAH cannot be directly determined as PAH interacts with the surface due to adhesion caused by an electrostatic interaction. The surface adsorption of 2° ADH (not shown) resulted in a frequency change of ~F=−36 Hz, which translates to a surface coverage 30 of 2.4×10$^{-12}$ mol cm$^{-2}$. The surface coverage is a characteristic of a densely packed monolayer of 2° ADH. Assuming that a single ADH molecule has a footprint of nm$^2$, an ordered densely packed monolayer of the enzyme would exhibit a maximum surface coverage, $\Gamma_{max}$=3.5×10-12 mol cm$^{-2}$, and this value translates to a surface coverage of 2.4×10$^{-12}$ mol cm$^{-2}$ for a randomly packed monolayer, 69% ordered packing density. The surface coverage obtained for 2° ADH compares well with the surface coverage of a tightly packed monolayer of other proteins having similar dimensions and mass.

Enzyme Adsorption

Figure 3A:
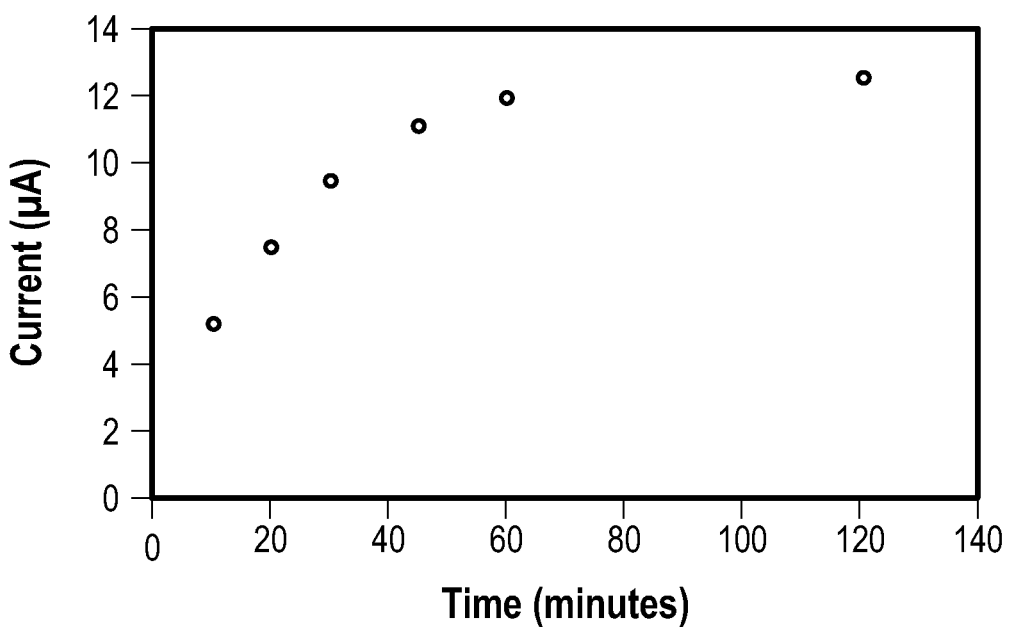
FIG. 3A shows the anodic peak current at different times of reconstitution.
Figure 3B:
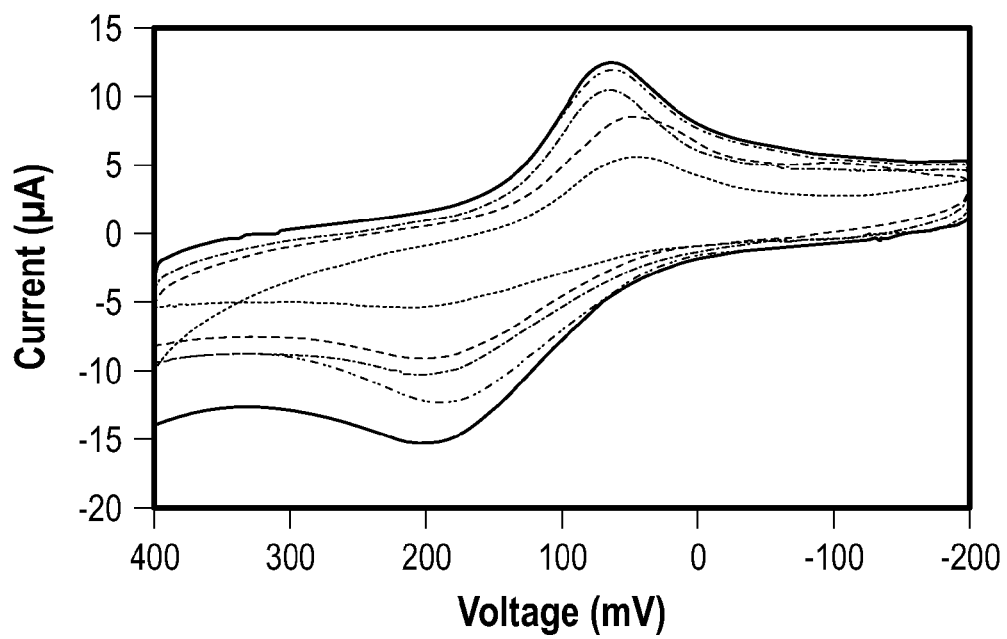
FIG. 3B is a graph showing the cyclic voltammograms of a biomimetic sensor in accordance with the invention at variable time intervals of 2° ADH adsorption.

FIG. 3B shows the cyclic voltammograms corresponding to the bioelectrocatlyitc currents corresponding to a constant 2-propanol concentration of 3.0×10$^{-2}$ M; at different times of adsorption. The anodic current increases with the reconstitution time to a saturation value after 1 h: FIG. 3A shows the anodic peak current at different times of reconstitution. The pseudo first order rate constant corresponding to reconstitution 15 calculated from this curve was 0.5 h-'.

Fluorescence microscopy and microcontact printing were used to establish the selective affinity of the 2° ADH to the NADP$^+$ co-factor. Initially, a PDMS stamp was used to create patterns of MPA on gold and than this patterned substrate was subjected to the same series of solutions (as discussed in the experimental section) to obtain MPA-TBO-PAH-CPA-NAD (P)$^+$ patterned gold substrate. This patterned substrate was then subjected to fluorescently labeled 2° ADH solution (2° ADH was labeled with FITC so it appears green) resulting in the selective affinity binding of the protein to the patterns. We believe NAD(P)$^+$ to be primarily responsible for this protein affinity as other control experiments when patterns were assembled in the absence of NAD(P)$^+$ showed poor selectivity.

Chronoamperometric Measurements

During the chronoamperometric experiments, the potential of the working electrode is stepped from −0.2 V to 0.3 V; the resulting current is measured as a function of time. 2-propanol in the vicinity of the TBO-PAH-CPA-NADP$^+$-2° ADH electrode is oxidized; the resulting electrons are transferred by the NADP$^+$ and TBO to the working electrode resulting in a measurable current. In such a case, an exponential model shown in Eq 4 may be used to model the chronoamperometric data. In this equation k'$_{et}$ and Q'$_{NADP}$ are the electron-transfer rate constant and the charge associated with oxidation following the step change in potential[47,48]. The surface coverage of each binding domain for NAD$^+$ ($\Gamma_{NAD}$) was determined using Eq 5; where n is the number of electrons transferred during the oxidation of 2-propanol (n=2), F is Faraday's constant, A the electrode area[48].

$$I = k'_{et} * Q'_{NAD} \exp(-K'_{et}t)$$

$$\Gamma_{NADP} = \frac{Q_{NAD}}{nFA}$$

The chronoamperometric current response of the PAH-TBO-CPA-NADP$^+$-2° ADH modified electrode was fit to Eq 8 using Origin 7.4 determining the values of $k'_{et}$ (80×10$^2$ s$^{-1}$) and the pre exponential factor ($k'_{et}$*Q=4.8×10$^{-4}$ A). The surface coverage of 2° ADH was determined to be $\Gamma_{NADP}$=2.1× 10$^{-12}$ mol cm$^{-2}$ which is similar to the value of $\Gamma_{NAD}$=2.7× 10$^{-12}$ mol cm$^{-2}$ estimated using QCM.

Figure 4:
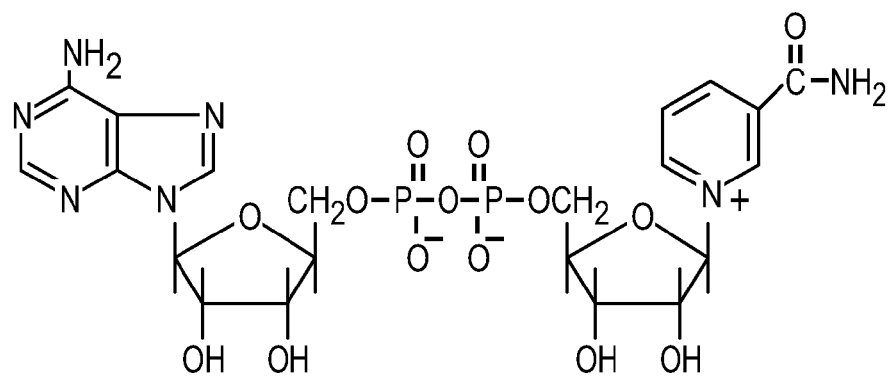
FIG. 4 is a drawing showing the chemical structure of $NAD^+$.

The possibility of linking co-factor units to the boronic acid-ligand attached to the gold electrode is not limited to NADP$^+$. Other cofactors such as flavin adenine dinucleotide (FAD) and β-Nicotinamide adenine dinucleotide (NAD$^+$) also contain ribose units that could be linked to the boronic acid ligand. However, as shown in FIG. 4, NAD$^+$ has two ribose units that could react with the phenylboronic acid ligand. Chronoamperometry was used to confirm these two different binding modes. The rate of change in current depends on the spatial orientation of the components making up the bioelectronic interface. As shown in FIG. 1, the phenylboronic acid group can bind to cis-diol of the cofactor unit {NAD(P)$^+$}. For this experiment a NAD$^+$ dependent mutant of *Thermoanaerobacter ethanolicus* 2° ADH (Y218D 2° ADH} was self-assembled onto TBO-PAH-NAD$^+$ electrodes. The transient current responses of this system can be described by Eq 6, where $k_{et}'$ and $k_{et}''$ are the electron-transfer constants for two differently positioned NADH cofactor units, and $Q_{NAD(P)H}'$ and $Q_{NAD(P)H}''$ are the charges associated with their oxidation upon the chronoamperometric experiment.

$$I=k'_{et}*Q'_{NAD}\exp(-k'_{et}t)+k''_{et}*Q''_{NAD}\exp(-k'_{et}t)$$

The current response of a potential step from the initial potential of −0.3V where the biocatalytic current is blocked to the final potential of 0.2 V where a transient biocatalytic current appears for the TBO-PAH-CPA-NAD$^+$-Y218D 2° ADH modified electrode (data not shown). The semi logarithimic plot decay of the faradaic current as a function of time follows a biexponential decay described by Eq 10 with electron transfer coefficients $k_{et}'$=1.04×10$^3$ s$^{-1}$ and $k_{et}''$=1.7×10$^2$ s$^{-1}$. From the pre-exponential factors we could also determine the ratio of charges associated with charge transfer; $Q_{NAD(P)H}'$~$Q_{NAD(P)H}''$, suggesting that the NAD$^+$ binds equally according to both of the possible ligation modes. The surface coverage, for the respective binding domains, was determined to be $\Gamma'_{NAD}$=2.1×10$^{-12}$ mol cm$^{-2}$ and $\Gamma''_{NAD}$=9.5×10$^{-13}$ mol cm$^{-2}$, indicating that the binding domain with the more rapid electron transfer is 2.2 times more common than the other domain. The total overall surface coverage for both domains was estimated to be $\Gamma_{NAD}$=3.1×10$^{-12}$ mol cm$^{-2}$.

Voltammetric Measurements

Figure 5:
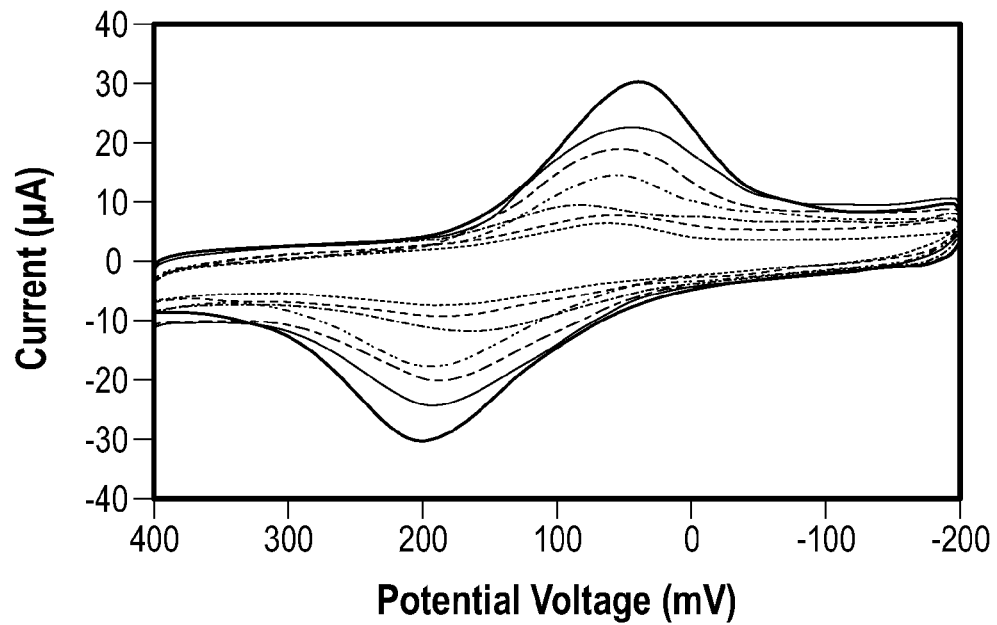
FIG. 5 is a graph of the cyclic voltammograms of an electrode in accordance with the invention functionalized with ADH, 2 h in the presence of difference concentrations of 2-propanol.

FIG. 5 shows the cyclic voltammograms of the enzyme-electrode at different 2-proponaol concentrations. The peak electrocatalytic anodic currents are indicative of the biocatalyzed oxidation reduction of 2-propanol. The anodic current begins at E=−150 mV (vs a standard Ag/AgCl reference electrode), the standard electrode, potential of TBO, suggesting that TBO mediates electron transfer between the NADP$^+$ redox center of the reconstituted enzyme[49,50]. The electrocatalytic currents increases linearly as the concentration of 2-propanol is elevated up to 4.0×10-2 M, and then it levels off. A calibration plot consisting of the peak anodic current plotted versus 2-propnaol concentration, at a constant potential, E=57 mV, in FIG. 5, inset. The anodic current increases linearly with the concentration of 2-propanol, indicating that the system functions as an 2-propanol biosensor. The sensitivity was found to be 0.75 µA cm$^{-2}$ mM$^{-1}$. Taking into account the saturation electrocatalytic current for the this system, $I_{cat}^{sat}$=31 µA, and the knowledge of the electrode area (A=0.5 cm$^2$) the surface coverage of the 2° ADH enzyme ($\Gamma_{NAD}$=2.1×10$^{-12}$ mol cm$^{-2}$) faradays constant (F=96,000 s A mol$^{-1}$) and the number of electrons transferred during the oxidation/reduction of the substrate (n=2) we estimated using Eq 11, the maximum turnover rate, TR$_{max}$, of the enzyme to be 152 s$^{-1}$ (the molecules of 2-propanol oxidized by one 2° ADH molecule per second).

$$TR_{max}=I_{cat}^{sat}/(Fn\Gamma_{ADH}A)$$

The calculated value of TR$_{max}$ was similar to that of the natural secondary alcohol dehydrogenase (2° ADH, ADEC 1.1.1.1 from *Thermoanaerohacter Ethanolicus*).

Figure 6:
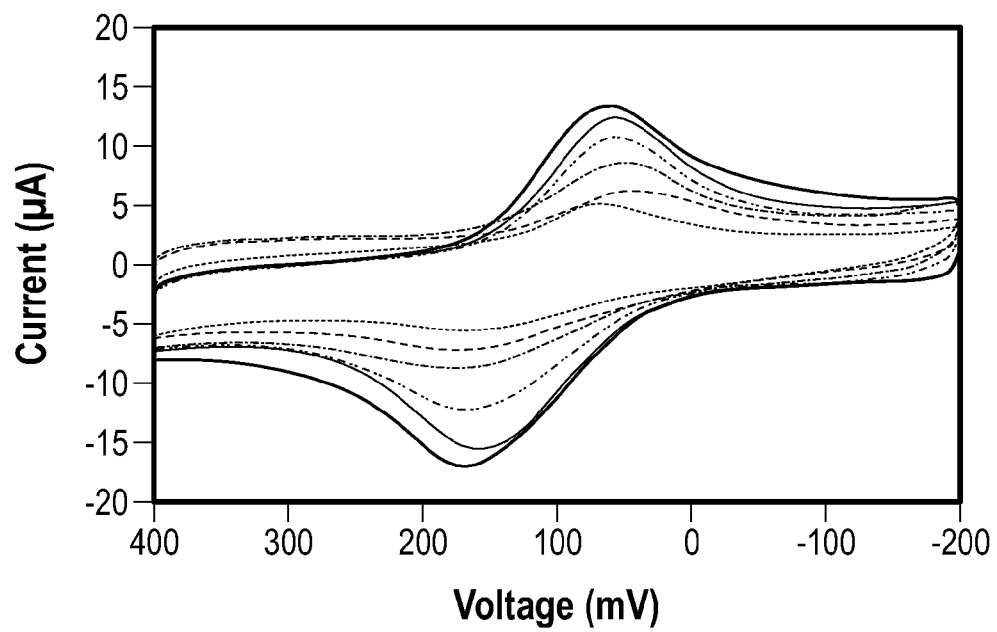
FIG. 6 is a graph showing the cyclic voltammograms of an electrode in accordance with the invention functionalized with 2° ADH, 3 h, in the presence of different concentrations of 2-propanol.
Figure 7:
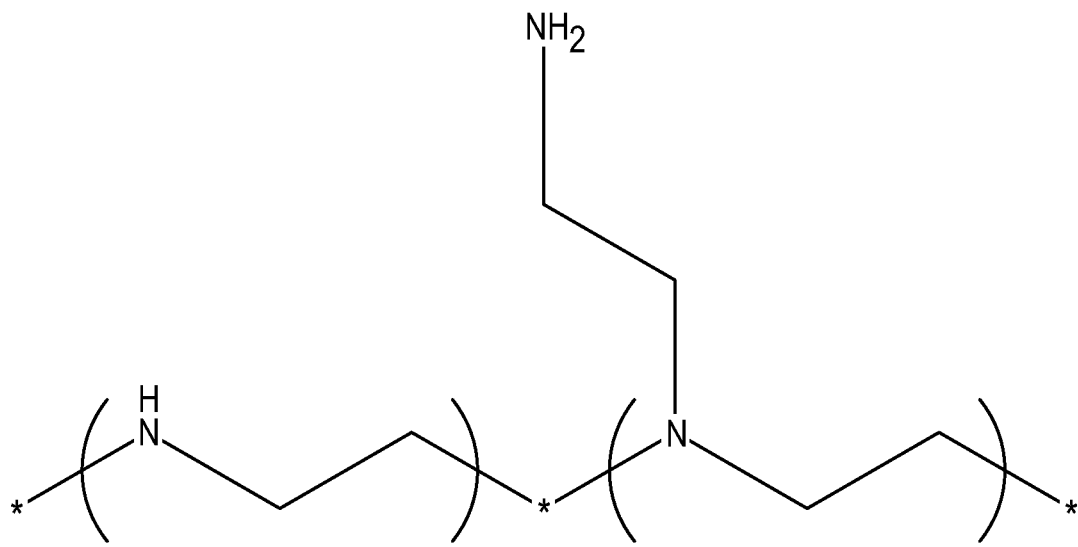
FIG. 7 is a drawing showing the structure of poly(ethyleneimine).

FIG. 6 shows the cyclic voltammograms of the reconstituted TBO-PAH-CPA NADP$^+$-Y218D 2° ADH-electrode at varying concentrations of 2-propanol. The peak electrocatalytic anodic currents are indicative of the biocatalyzed oxidation of 2-propanol. The anodic current begins at E=−75 mV (versus Ag/AgCl), the standard electrode potential of TBO, suggesting that TBO mediates electron transfer between the NADP$^+$ redox center of the reconstituted enzyme. FIG. 6, inset, shows the calibration plot corresponding to different concentrations of 2-propanol. The electrocatalytic currents increases linearly as the concentration of 2-propanol is elevated up to 4.0×10$^{-2}$ M, and then it levels off due to the saturation of the enzyme. Knowing the saturated current for the this system, $I_{cat}^{sat}$=14 µA, and the knowledge of the electrode area the surface coverage of the Y218D 2° ADH enzyme, $\Gamma_{NAD}$=3.1×10$^{-12}$ mol cm$^{-2}$, faradays constant, F=96,000 s A mol$^{-1}$ and the number of electrons transferred during the oxidation/reduction of the substrate (n=2) we estimated using Eq 11, the maximum turnover rate, TR$_{max}$, of the enzyme to be 47 s$^{-1}$.

Stability Determination

The integrated NADP$^+$-2° ADH electrode lost approximately 15% of its activity upon operation for 24 h under ambient conditions (25±2° C., atmospheric pressure). On the other hand, the integrated NAD$^+$-Y218D-2° ADH electrodes degraded by 10% on continuous operation for 24 h. However, these electrodes do reveal high stability upon their storage in the phosphate buffer, pH=7.4 at ambient temperature and pressure. Under these conditions, no observable degradation of the enzyme-electrodes was detected after storage for a period of 2 weeks. The stability of the resulting electrodes and particularly the integrated nature of the NAD(P)$^+$ dependent electrodes do not reveal any leakage of the cofactors, suggesting that such electrodes could be applied as biosensors or possibly as the active elements of biofuel cells. This electrode was designed for the thermostable biocatalytic oxidation of 2-propanol; however, this design also provides an opportunity for the biocatalytic oxidation of secondary alcohols with NAD$^+$ as the cofactor.

Conclusions:

Efficient electrical coupling of NAD(P)$^+$ dependent wild type 2° ADH and NAD$^+$ dependent mutant of 2° ADH has been achieved. QCM studies provided evidence for the assembling of the desired bioelectronic interface. Cyclic Voltammetry confirmed electrical communication between the redox centers of the enzymes, the electron mediator and the electrodes. This system was then tested for sensing applications as a potential isopropyl sensor and linear response up to 40 mM was achieved. Fluoresence microscopy and atomic force microscopy were also used to further characterize the interface and to check the feasibility of the proposed approach. This new method turns the preparation of NAD(P)+ dependent enzyme based electrodes into an easy practice at a considerably lower cost. Further studies involving the use of other polyelectrolytes and proteins are currently underway.

EXPERIMENTAL SECTION 2

Chemicals

*Escherichia Coli* (DH5α) containing the wild-type and G198C 2° alcohol dehydrogenase *Thermoanaerobacter ethanolicus* (sADH) recombinant plasmids were grown in rich complex media (20 g/L tryptone, 10 g/L yeast extract, 5 g/L NaCl) according to published procedures (SOURCE). Tryptone and yeast extract were purchased from Fisher Scientific. Fluoroscein isothiocyanate (FITC) was purchased from Molecular Probes (Eugene, Oreg.). Cofactors for sADH, 3-nicotinamide adenine dinucleotide phosphate ($NADP^+$) and β-nicotinamide adenine dinucleotide ($NAD^+$) were purchased from Sigma Aldrich. All other materials, including polyethylenimine (PEI), 3-mercaptopropionic acid (MPA), toluidine blue O (TBO), N-hydroxysuccinimide (NHS), 1-ethyl-3-(3-dimethylaminopropyl)carbodiimide (EDC), 3-carboxyphenyl boronic acid, and isopropanol were obtained from Sigma Aldrich. Ultrapure water (18.2 MΩ) was supplied by a Barnstead Nanopure-UV four-stage purifier equipped with a UV source and a 0.2 μm filter (Barnstead International Dubuque, Iowa).

Electrode Modification

Gold electrodes (10 mm by 11 mm rectangular electrodes, roughness factor 1.2) were used for modifications. The gold electrodes were cleaned by boiling in piranha solution (70% sulfuric acid-30 % hydrogen peroxide) for 1 min. The electrodes were then washed with de-ionized water, dried under nitrogen and stored in concentrated sulfuric acid. Prior to modification, the electrodes were rinsed thoroughly with water and dried under nitrogen. A cyclic voltammogram was recorded in 1 M $H_2SO_4$ to evaluate surface cleanliness. The clean gold electrodes were then soaked in a 0.05 M 3-mercaptopropionic acid solution in ethanol for 4 hr and then rinsed with ethanol and de-ionized water, leaving a self-assembled monolayer (~5 Å thickness) of 3-mercaptopropionic acid on the gold electrode. The electrodes were incubated for 2 h in a solution of 10 mM NHS in the presence of 5 mM EDC and reacted with TBO in 0.1 M phosphate buffer, pH=7.4. The modified electrodes were then rinsed with de-ionized water and soaked in 10 mM PAH solution prepared in HEPES buffer containing 0.1 M NaCl, pH 7.4. A PAH monolayer self-assembled on the 3-mercaptopropanoic acid-TBO functionalized electrode, due to the ionic interactions between the positively charged amine groups of the PAH and the carboxylate ions of the 3-mercaptopropionic acid monolayer. The PAH functionalized electrodes were then reacted with 3-carboxyphenyl boronic acid (BA) in the presence of 5 mM EDC and 10 mM NHS in phosphate buffer, pH=7.4. The gold electrodes functionalized with boronic acid were further functionalized with $NAD^+$ and $NADP^+$ cofactors. The functionalized gold electrodes were reacted with 5 mM solution of the respective cofactor in phosphate buffer, pH 7.4, for 2 h, and then washed with water. The TBO $NADP^+$ and TBO-$NAD^+$ functionalized gold electrodes were then reacted with 4.4 mg mL$^{-1}$ SADH and 5.3 mg mL$^{-1}$ G198C sADH, respectively, in 0.1 M phosphate buffer, pH=7.4 for 2 h (unless otherwise stated) at room temperature, briefly washed with water, then reacted with 25% (v/v) glutaric dialdehyde in water for 20 min. The electrodes were then washed with water and used for the bio-catalytic oxidation of isopropanol.

Preparation of PDMS Stamps

An elastomeric stamp is prepared by curing poly(dimethylsiloxane) (PDMS) on a microfabricated silicon master, which acts as a mold, to allow the topography of the stamp to form a negative replica of the master. The PDMS stamps were made by pouring a 10:1 solution of the elastomer and initiator over a prepared silicon master. The silicon master was pretreated with flourosilanes to facilitate the removal of the PDMS from the silicon master. The solution was allowed to cure overnight at 60C. The masters were prepared in the Microsystems Technology Lab at MIT and consisted of features (parallel lines and circles) from 1 to 10 pm.

Fluorescent Labeling of Protein

A 5.5 mg sample of sADH, in 2 mL Tris buffer, pH=5.8, was dialyzed against a 1 M sodium bicarbonate solution, pH=9, for 24 h. The bicarbonate solution was changed every 6 h during the dialysis process. One hundred microliters of dimethyl sulfoxide (DMSO) was combined with 0.05 mg FITC. The DMSO-FITC solution was then added to the protein solution, and continuously stirred in the dark for 2 h. The protein was then dialyzed against de-ionized water for 24 h, changing the water every 6 h, to remove excess FITC.

Electrochemical Measurements

A conventional three-electrode system consisting of the enzyme-modified gold working electrode, a platinum auxiliary electrode, and a saturated silver/silver chloride (Ag/AgCl) reference electrode isolated by a glass flit, were used for the electrochemical measurements, All potentials are reported against the saturated Ag/AgCl reference electrodes. The electrochemical cell was placed into a grounded Faraday cage (Bioanalytical Systems, BAS, West Lafayette, Ind., C-3 cell stand). Cyclic voltammetry and chronoamperometry were performed using an electrochemical analyzer composed of a potentiostat/galvanostat (BAS CV-50W) connected to a computer (BAS CV-50W Version 2.3).

Microgravitational Measurements

A Quartz Crystal Microbalance (QCM) analyzer (5 MHz crystals, Maxtek, Research Quartz Crystal Microbalance, Santa Fe Springs, Calif.) linked to a computer running RQCM® data logging software was used for microgravimetric measurements, Quartz crystals were sandwiched between two gold electrodes (geometrical area 1.26 cm$^2$, roughness factor ca. 0.9). The gold electrode surfaces were washed and modified as described previously. Frequency changes of the quartz crystals were measured, once a baseline oscillation frequency was obtained using a HEPES buffer, pH 7.4, in 10 mM HEPES buffer to track changes in mass during each step of the interface assembly. All the measurements were carried out at ambient temperature (22±2.0° C.).

Other Techniques

Fluorescence images were obtained using a Nikon Eclipse E 400 microscope (Nikon, Melville, N.Y.). Atomic force microscopy (AFM) images were obtained in air with a Nanoscope IV multimode scope (Digital Instruments, Santa Barbara, Calif.). The AFM was equipped with tapping-mode etched silicon probes. 3-mercaptopropanoic acid was stamped on to a gold surface using a polydimethylsiloxane (PDMS) stamp according to published procedures (SOURCE), and the resulting patterned gold electrode was modified according to the procedure described above. The resulting patterned TBO-PAH-NAD(P)$^+$ electrodes were dipped in the fluorescently labeled sADH solutions for 1 hr and then viewed under the fluorescence microscope. The thickness of the micro-patterned films was determined using cross-sectional analysis of the AFM images. An ellipsometer (WVASE 32, J.A. Woollam Co. Inc., Lincoln Nebr.) was used to measure thickness of the layers added to the electrode.

Results and Discussion

A carboxylic acid monolayer was self-assembled on the gold electrode and activated in the presence of N-hydroxysuccinimide. Toluidine blue was then reacted with this monolayer to form an active layer for electron mediation. The resulting layer was then reacted with PEI, to form an active layer of primary amines. β-nicotinamide adenine dinucleotide phosphate (NAD(P)$^+$) was then reacted with primary amines on PEI using a boronic acid linkage. Affinity binding of secondary alcohol dehydrogenase (sADH) on the resulting interface yielded an isopropyl alcohol biosensor.

Figure 8:
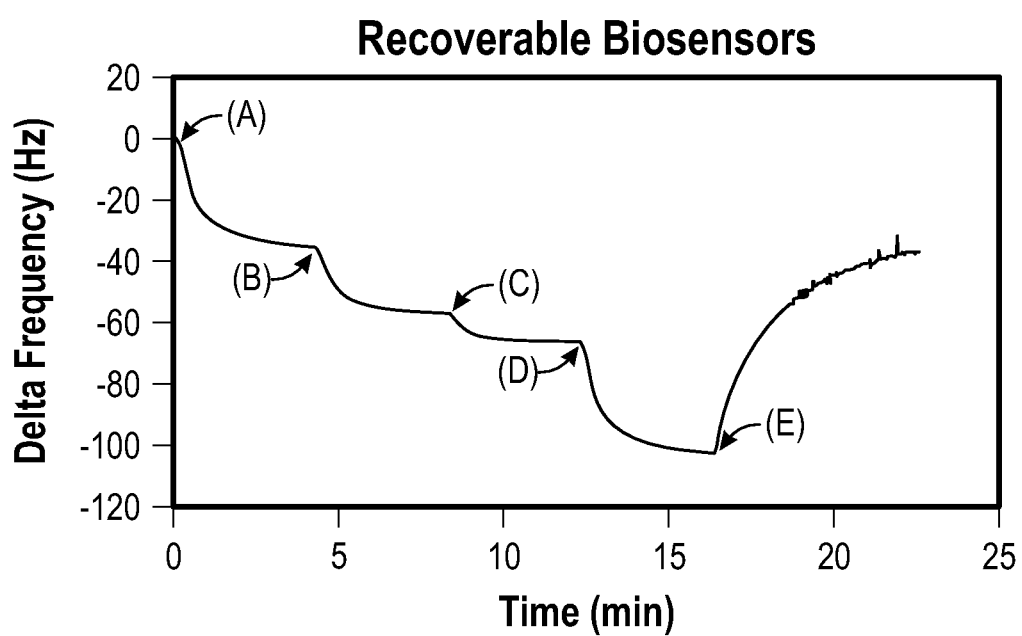
FIG. 8 is a graph showing the quartz crystal microbalance for the addition of (A) toluidine blue, (B) carboxyphenyl boronic acid modified PEI, (C)$NAD(P)^+$, (D) secondary alcohol dehydrogenase, and (E) after lowing the pH of the system.

Quartz crystal microbalance was used to track the assembly of the bioelectronic interface. With QCM, the oscillation frequency of a gold-coated quartz crystal is measured before and during the adsorption of the monolayer onto the surface. The resulting frequency change (ΔF, hertz) can be related to the amount of material, (ΔM, grams), by the Sauerbrey Equation. (Eq. 1)

$$\Delta F = \frac{-f_0^2 \Delta M}{A\sqrt{\mu\rho}}$$

where $f_0$ is the fundamental resonant frequency of the quartz crystals (5 MHz), μ is the shear modulus of the quartz (2.94× $10^{11}$ g cm$^{-1}$ s$^{-2}$), ρ is the density of the crystal (2.648 g cm$^{-3}$), and A represents the geometric surface area of the electrode (1.26 cm$^2$). Once a baseline frequency was obtained, (a) 5 mM TBO, (b) 1 mM PEI, (c) 1 mM NAD(P)$^+$, and (d) 4.4 mg/ml SADH were introduced into the measuring cell sequentially. FIG. 8, shows the QCM images indicating the change in frequency (ΔHz) arising from the addition of these compounds. The average frequency change was −35, −22, −9 and 36 Hz respectively. As can be seen in FIG. 8, reducing the pH of the solution inside the measuring cell to 2 by the addition of 0.01 M HCl results in a positive frequency change of approx. 65 Hz, suggesting the desorption of some layers. An MPA monolayer on the gold surface contains multiple carboxylic groups; the degree of protonation of these groups can be controlled. The protonated carboxylic groups were used to bind TBO while the negatively charged carboxylate groups served as anchor sites for bonding to PEI. On lowering the pH of the solution, we believe most of the carboxylate groups on the MPA become protonated, thus considerably reducing the electrostatic interactions between the MPA and PEI and as a result causing the desorption of PEI and all other layers adsorbed or covalently linked to PEI. The TBO layer should remain intact. The frequency change (65 Hz), as seen in FIG. 8 (step e), is approximately equal to the frequency change expected if all layers except TBO are desorbed, thus supporting our hypothesis. Moreover, similar QCM curves (data not shown) were obtained on subjecting the same electrode to more cycles of assembly and desorption.

Fluorescence microscopy and microcontact printing were also used to study the effect of lowering of pH on the adsorbed layers. Initially a PDMS stamp was used to create patterns of MPA on gold and than this patterned substrate was subjected to series of solutions (as described in detail in the experimental section) to obtain NAD(P)$^+$-PEI-TBO-MPA patterned gold substrate. This patterned substrate was then subjected to fluorescently labeled protein solution resulting in the selective affinity binding of the protein to the patterns. Washing this substrate in a low pH solution results in desorption of different layers including the protein layer as indicated by the reduction in fluorescence. Moreover, almost complete fluorescence recovery, was observed when this substrate was subjected again to the same series of solutions. These results suggest that we can regenerate this assembly repeatedly.

Figure 9:
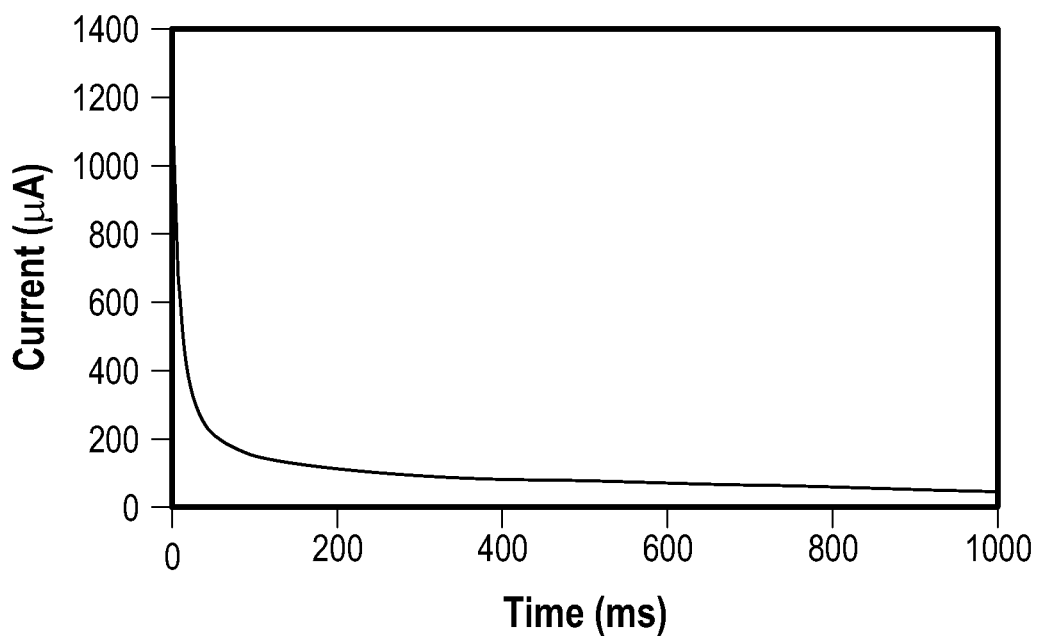
FIG. 9 is a chronoamperometric graph of current versus time for the integrated enxyme-electrode obtained by cross-linking of secondary alcohol dehydrogenase associated with a TBO-PEI-phenylboronic acid-$NADP^+$-functionalized electrode in the presence of isopropanol.

The electrocatalytic activity of the composite system was kinetically determined using chronoamperometry. The complexity of the present system originates from the fact that the NAD(P)$^+$ cofactors are not electrochemically active by themselves and their potentiometric response cannot be directly measured unlike other cofactors such as FAD. However the whole system MPA-TBO-PEI-NAD(P)$^+$-sADH in the presence of isopropanol produces current upon the application of a sufficiently positive potential. In this formation, there is an enzymatic reduction of NAD(P)$^+$ to NAD(P)H that is further oxidized by TBO. The transient bioelectrocatalytic anodic current produced by TBO-PEI-NADP$^+$-sADH electrode should have monoexponential kinetics due to a single binding mode of NADP$^+$. The interfacial electron transfer coefficient, $k_{et}'$, for the NADP$^+$ co-factor unit can be described by eq. 2.

$$I = k'_{et} * Q''_{NAD} \exp(-k'_{et} t)$$

Where $K_{et}$, is the electron transfer constant, $Q_{NAD}$, is the charge associated with the oxidation of NAD(P)H upon the application of the potential step. The surface coverage of the NADP$^+$, $\Gamma_{NAD}$, can be determined using eq. 3.

$$\Gamma_{NAD} = \frac{Q_{NAD}}{nFA}$$

Where A is the electrode area, n is the number of electrons transfer during oxidation, n=2 and F is the faraday constant. FIG. 9, shows the current response of a potential step from the initial potential of −0.3 V where the biocatalytic current is blocked to the final potential of 0.4 V where a transient biocatalytic current appears for the PEI-TBO-NADP$^+$-sADH modified electrode. The resulting time dependent current decay in a semi-log plot, revealed uniexponential decay with an electron transfer coefficient of $k_{et}$=9.9×10$^4$ s$^{-1}$ and charge, $Q_{NAD(P)H}$=7.0×10$^{-8}$ s*A, corresponding to a surface coverage of 9.16×10$^{-13}$ mol cm$^{-2}$.

Figure 10:
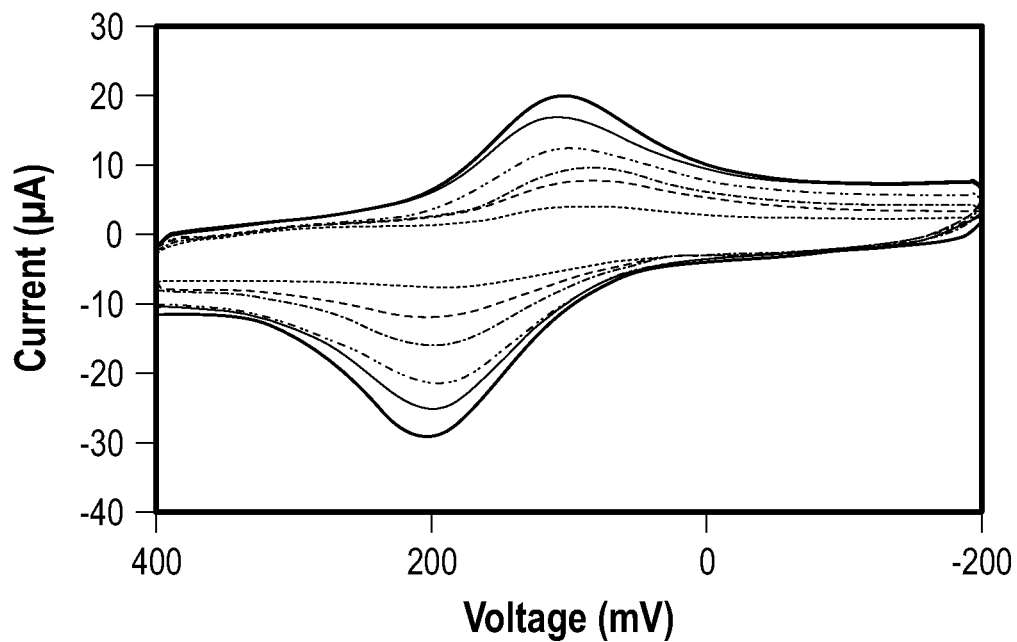
FIG. 10 is a graph showing the cyclic voltammograms of the TBO-PEI-phenylboronic acid-functionalized gold electrode reconstituted with secondary alcohol dehydrogenase in the presence of different concentrations of isopropanol.

Cyclic voltammetry was used to establish electrical coupling between the enzyme and the electrode. FIG. 10 shows cyclic voltammograms at a constant isopropanol concentration of 30 mM, at different times of reconstitution. The anodic current increases with the reconstitution time to a saturation value after 1 h. The pseudo first order rate constant corresponding to reconstitution calculated from this curve was 0.5 h$^{-1}$. The peak electrocatalytic anodic currents are indicative of the biocatalyzed oxidation/reduction of isopropanol. The anodic current begins at E=150 mV, versus standard Ag/AgCl reference electrode, suggesting that TBO mediates electron transfer between the NADP$^+$ redox center of the reconstituted enzyme. The electrocatalytic current was shown to increase linearly with the concentration of the isopropanol; to approximately 40 mM.

Taking into account the saturation electrocatalytic current for the NADP$^+$-sADH system, $I_{cat}^{sat}$=42 μA, and the knowledge of the electrode area, A=0.4 cm$^2$, the surface coverage of the sADH enzyme, $\Gamma_{NAD}$=9.16×10$^{-13}$ mol cm$^{-2}$, faradays constant, F=96,000 s*A mol$^{-1}$ and the number of electrons transferred during the oxidation/reduction of the substrate, n=2, we estimated using eq. 3, the maximum turnover rate, $TR_{max}$, of the enzyme to be 600 s$^{-1}$ (the molecules of isopropanol oxidized by one sADH molecule per second).

$$TR_{max}=I_{cat}{}^{sat}/(Fn\Gamma_{ADH}A)$$

The calculated value of $TR_{max}$ was found to be similar to that of the natural secondary alcohol dehydrogenase (sADH, ADBC 1.1.1.1 from *Termoanaerobacter Ethanolicus*) with its native $O_2$ electron acceptor.

The proposed enzyme electrode is irreversible or stable at normal pH range. On washing with low pH solution, the current response to different isopropanol concentrations returns nearly to zero due to the removal of adsorbed layers. However, on subjecting it again to the same series of solutions, the current response returns nearly to the original value. These results suggest the isopropanol sensor made using this self-assembly can be used repeatedly.

The stability of the electrodes is a major concern: the integrated NADP$^+$-sADH electrode lost approximately 15% of its activity upon operation for 24 h under ambient conditions (25±2° C., atmospheric pressure). The integrated NAD$^+$-sADH electrodes reveal 10% degradation upon operation under ambient conditions upon the operation for 24 h. The electrodes do reveal high stability upon their storage in the phosphate buffer, pH=7.4 at ambient temperature and pressure. Under these conditions, no observable degradation of the enzyme-electrodes was detected after storage for a period of 2 weeks. The stability of the resulting electrodes and particularly the integrated nature of the NAD(P)$^+$ dependent electrodes did not reveal any leakage of the cofactors, suggesting that such electrodes could be applied as biosensors or possibly as the active elements of biofuel cells. This electrode was designed for the thermostable biocatalytic oxidation of isopropanol; however, this design also provides an opportunity for the biocatalytic oxidation of secondary alcohols with NAD(P)$^+$ as the cofactor.

A novel self assembly technique for the fabrication of an isopropanol sensor based on polyelectrolyte has been described. QCM and fluorescence microscopy provided evidence for the renewability of the proposed interface while cyclic voltammetry confirmed electrical communication between the redox centers of the enzymes, the electron mediator and the electrodes. The resulting isopropanol sensor showed reproducible linear response up to 40 mM and was quite stable. The self assembly method was also found to have little effect on the activity of the enzyme; the sensor showed higher sensitivity compared with other conventional covalent immobilization methods. Another advantage of this enzyme electrode is that washing with a solution of extreme pH can regenerate it repeatedly. This new method turns the preparation of NAD(P)$^+$ dependent enzyme based electrodes into an easy practice at a considerably lower cost. Further studies involving the use of other polyelectrolytes and proteins are currently underway.

The above description is considered that of the preferred embodiment(s) only. Modifications of the invention will occur to those skilled in the art and to those who make or use the invention. Therefore, it is understood that the embodiment(s) shown in the drawings and described above are merely for illustrative purposes and not intended to limit the scope of the invention, which is defined by the following claims as interpreted according to the principles of patent law, including the doctrine of equivalents.

The invention claimed is:

1. A bioelectronic device comprising:
   an electrically conductive substrate;
   an electron-carrying mediator chemically bound to the electrically conductive substrate;
   a polyelectrolyte electrostatically bound to the electrically conductive substrate via the electron-carrying mediator; and
   a chemical composite comprising a biologically active compound bound, directly or indirectly, to the polyelectrolyte via an enzyme cofactor chemically bonded to the polyelectrolyte, wherein the bioelectronics device is without a bi-functional co-factor, and wherein the biologically active compound is an enzyme.

2. The device of claim 1, wherein the enzyme is a redox enzyme.

3. The device of claim 1, wherein the biologically active compound is a redox enzyme which is indirectly bound to the polyelectrolyte.

4. The device of claim 3, wherein the enzymatic cofactor is bonded indirectly to the polyelectrolyte via hydrogen bonding with a boronic acid group of a moiety covalently bonded to the polyelectrolyte.

5. The device of claim 1, wherein the enzyme is a hydrogenase.

6. A regenerable bioelectronic device comprising:
   an electron-carrying mediator chemically bound to electrically conductive substrate; and
   a chemical composite comprising a biologically active compound coupled to a polyeletrolyte via an enzyme cofactor chemically bonded to the polyelectrolyte, wherein the biologically active compound is reversibly bound to the chemically modified substrate by electrostatic forces, wherein the regenerable bioelectronics device is without a bi-functional co-factor, and wherein the biologically active compound is an enzyme.

7. The device of claim 6, wherein the enzyme is a redox enzyme.

8. The device of claim 6, wherein the biologically active compound is a redox enzyme which is indirectly bound to the polyelectrolyte.

9. The device of claim 8, wherein the enzymatic cofactor is bonded indirectly to the polyelectrolyte via hydrogen bonding with a boronic acid group of a moiety covalently bonded to the polyelectrolyte.

10. The device of claim 6, wherein the enzyme is a hydrogenase.

* * * * *

UNITED STATES PATENT AND TRADEMARK OFFICE
CERTIFICATE OF CORRECTION

PATENT NO. : 8,435,773 B2
APPLICATION NO. : 11/914340
DATED : May 7, 2013
INVENTOR(S) : Robert M. Worden et al.

Page 1 of 2

It is certified that error appears in the above-identified patent and that said Letters Patent is hereby corrected as shown below:

In the Specifications

Col. 1/Line 48: reads as ", ability" and should read as ", or ability"
Col. 1/Line 49: reads as "Secondary 30 alcohol" and should read as "Secondary alcohol"
Col. 1/Line 60: reads as "oxidation 5 and" and should read as "oxidation and"
Col. 1/Line 61: reads as "(P)+are" and should read as "(P)+ are"
Col. 1/Line 67: reads as "and 10 the" and should read as "and the"

Col. 2/Line 6: reads as "of a" and should read as "of"
Col. 2/Line 8: reads as "and 15 toluidine" and should read as "and toluidine"
Col. 2/Line 27: reads as "electrode by" and should read as "electrode can be assembled by"
Col. 2/Line 55: reads as "prevented" and should read as "prevents"

Col. 3/Line 23: reads as "of toluidine" and should read as "of (a) toluidine"
Col. 3/Line 24: reads as ",(b)" and should read as ", (b)"
Col. 3/Line 24: reads as "mM," and should read as "mM"
Col. 3/Line 25: reads as "NADP+in" and should read as "NADP+ in"
Col. 3/Line 47: reads as "(C)NAD(P)+" and should read as "(C) NAD(P)+"

Col. 4/Line 25: reads as "chip," and should read as "chip."

Col. 6/Line 42: reads as "require a" and should read as "requires a"
Col. 6/Line 46: reads as "and .me of" and should read as "and ease of"
Col. 6/Line 56-57: reads as ""{Polyclectrolyte" and should read as ""Polyclectrolyte"
Col. 6/Line 60: reads as "nanoparticles Tn" and should read as "nanoparticles. In"
Col. 6/Line 67: reads as "-poly(3,4-dihydroxybenzaldehyde," and should read as "poly (3,4-dihydroxybenzaldehyde),"

Col. 7/Line 3: reads as "of a generic" and should read as "of generic"

Signed and Sealed this
Seventh Day of January, 2014

Margaret A. Focarino
*Commissioner for Patents of the United States Patent and Trademark Office*

CERTIFICATE OF CORRECTION (continued)
U.S. Pat. No. 8,435,773 B2

Col. 7/Line 5: reads as ", facilitate" and should read as ", also facilitate"
Col. 7/Line 15: reads as "electrode;" and should read as "electrode,"
Col. 7/Line 17: reads as "complete" and should read as "completes"
Col. 7/Line 19: reads as "prevented" and should read as "prevent"
Col. 7/Line 23: reads as "to -functional" and should read as "tri-functional"
Col. 7/Line 24: reads as "with out" and should read as "without"
Col. 7/Line 42: reads as "limiting therefore" and should read as "limiting. Therefore,"
Col. 7/Line 53: reads as "NAD(P)H," and should read as "NAD(P)H"
Col. 7/Line 63: reads as "addresses" and should read as "address"

Col. 8/Lines 1-2: reads as "polyelectrolyetes such" and should read as "polyelectrolyetes, such"
Col. 8/Line 10: reads as ". By varying" and should read as ". Varying"
Col. 8/Line 10: reads as "pH provides" and should read as "pH"

Col. 9/Lines 4-5: reads as "generally," and should read as "general,"
Col. 9/Line 28: reads as "limiting of" and should read as "limiting, of"

Col. 11/Line 44: reads as "(," and should read as "),"

Col. 12/Line 5: reads as "microbalance, QCM" and should read as "microbalance (QCM)"
Col. 12/Line 12: reads as "NAD(P)+respectively." and should read as "NAD(P)+, respectively"
Col. 12/Line 34: reads as "M; at" and should read as "M at"
Col. 12/Line 36: reads as "h: FIG." and should read as "h. FIG."

Col. 16/Line 33: reads as "measurements," and should read as "measurements."